United States Patent
Nagashima et al.

(10) Patent No.: US 9,884,316 B2
(45) Date of Patent: Feb. 6, 2018

(54) MONONUCLEAR RUTHENIUM COMPLEX AND ORGANIC SYNTHESIS REACTION USING SAME

(71) Applicants: KYUSHU UNIVERSITY, NATIONAL UNIVERSITY CORPORATION, Fukuoka-shi, Fukuoka (JP); SHIN-ETSU CHEMICAL CO., LTD., Tokyo (JP)

(72) Inventors: Hideo Nagashima, Fukuoka (JP); Yusuke Sunada, Fukuoka (JP); Hajime Ogushi, Fukuoka (JP); Koji Sakuta, Annaka (JP)

(73) Assignees: KYUSHU UNIVERSITY, NATIONAL UNIVERSITY CORPORATION, Fukuoka-shi (JP); SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/124,773

(22) PCT Filed: Mar. 3, 2015

(86) PCT No.: PCT/JP2015/056200
§ 371 (c)(1),
(2) Date: Sep. 9, 2016

(87) PCT Pub. No.: WO2015/137194
PCT Pub. Date: Sep. 17, 2015

(65) Prior Publication Data
US 2017/0056872 A1    Mar. 2, 2017

(30) Foreign Application Priority Data

Mar. 10, 2014 (JP) ................. 2014-046121

(51) Int. Cl.
*C07C 69/38* (2006.01)
*B01J 31/16* (2006.01)
(Continued)

(52) U.S. Cl.
CPC ............ *B01J 31/1608* (2013.01); *C07C 5/03* (2013.01); *C07C 67/283* (2013.01); *C07C 67/303* (2013.01); *C07C 209/50* (2013.01); *C07C 209/62* (2013.01); *C07F 7/0829* (2013.01); *C07F 7/0879* (2013.01); *C07F 15/0046* (2013.01); *C07F 15/0053* (2013.01); *C07F 19/00* (2013.01); *B01J 2231/323* (2013.01); *B01J 2231/645* (2013.01); *B01J 2531/821* (2013.01); *C07C 2101/14* (2013.01); *C07C 2102/08* (2013.01); *C07C 2531/16* (2013.01); *C07C 2531/18* (2013.01)

(58) Field of Classification Search
USPC ........................ 556/136, 140, 415
See application file for complete search history.

(56) References Cited

U.S. PATENT DOCUMENTS

| | | | |
|---|---|---|---|
| 4,309,558 A | 1/1982 | Koga et al. | |
| 5,248,802 A | 9/1993 | Bank | |

(Continued)

FOREIGN PATENT DOCUMENTS

| | | |
|---|---|---|
| DE | 28 10 032 A1 | 9/1978 |
| EP | 0 403 706 A2 | 12/1990 |

(Continued)

OTHER PUBLICATIONS

Hill; Organometallics; 2010, 29(4), 1026-1031.*

(Continued)

*Primary Examiner* — Pancham Bakshi
(74) *Attorney, Agent, or Firm* — Birch, Stewart, Kolasch & Birch, LLP

(57) ABSTRACT

A neutral or cationic mononuclear ruthenium divalent complex represented by formula (1) can actualize exceptional catalytic activity in at least one reaction among a hydrosilylation reaction, hydrogenation reaction, and carbonyl compound reduction reaction.

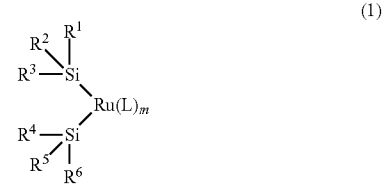

(1)

Figure 1:
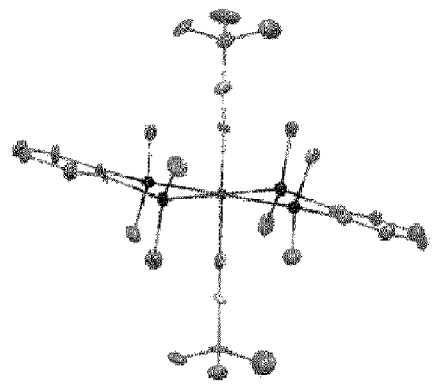

(In the formula, $R^1$-$R^6$ each independently represent a hydrogen atom or an alkyl group, aryl group, aralkyl group, organooxy group, monoorganoamino group, diorganoamino group, monoorganophosphino group, diorganophosphino group, monoorganosilyl group, diorganosilyl group, triorganosilyl group, or organothio group optionally substituted by X; at least one pair comprising any of $R^1$-$R^3$ and any of $R^4$-$R^6$ together represents a crosslinkable substituent; X represents a halogen atom, organooxy group, monoorganoamino group, diorganoamino group, or organothio group; L each independently represent a two-electron ligand other than CO and thiourea ligands; two L may bond to each other; and m represents an integer of 3 or 4.)

13 Claims, 4 Drawing Sheets

(51) Int. Cl.
| | |
|---|---|
| C07C 209/50 | (2006.01) |
| C07F 15/00 | (2006.01) |
| C07F 19/00 | (2006.01) |
| C07C 5/03 | (2006.01) |
| C07C 67/303 | (2006.01) |
| C07C 67/283 | (2006.01) |
| C07C 209/62 | (2006.01) |
| C07F 7/08 | (2006.01) |

(56) References Cited

U.S. PATENT DOCUMENTS

| | | |
|---|---|---|
| 5,559,264 A | 9/1996 | Bowman et al. |
| 2004/0092759 A1 | 5/2004 | Westmeyer et al. |
| 2009/0171056 A1 | 7/2009 | Hofmann et al. |

FOREIGN PATENT DOCUMENTS

| | | |
|---|---|---|
| JP | 5032561 B2 | 9/2012 |
| JP | 2013-178968 A | 9/2013 |
| WO | WO 96/05207 A1 | 2/1996 |

OTHER PUBLICATIONS

Dorwald, Side Reactions in Organic Synthesis, 2005, Wiley: VCH Weinheim Preface, pp. 1-15 & Chapter 8, pp. 279-308.*

Atheaux et al., "Exchange Processes in Complexes with Two Ruthenium ($\eta^2$-Silane) Linkages: Role of the Secondary Interactions between Silicon and Hydrogen Atoms", Organometallics, vol. 21, 2002, pp. 5347-5357.

Brown, Weldon G., "Reductions by Lithium Aluminum Hydride", Organic Reactions, vol. 6, Chapter 10, Mar. 15, 2011, pp. 469-493.

Burgio et al., "Facile Synthesis and Structures of $\eta^6$-Arene Bis(silyl) Complexes of Ruthenium(II): ($\eta^6$-arene)Ru(PPh$_3$)(SiX$_3$)$_2$", Organometallics, vol. 22, No. 24, 2003, pp. 4928-4932.

Chan et al., "Syntheses and Characterization of Hydrotris(1-pyrazolyl)borate Dihydrogen Complexes of Ruthenium and Their Roles in Catalytic Hydrogenation Reactions", Organometallics, vol. 16, No. 1, 1997, pp. 34-44.

Corella II et al., "(Isocyanide)ruthenate Analogues of Tetracarbonylferrate", Angewandte Chemie International Edition in English, vol. 31, No. 1, 1992, pp. 83-84.

Delpech et al., "Ruthenium Complexes Containing Two Ru—($\eta^2$—Si—H) Bonds: Synthesis, Spectroscopic Properties, Structural Data, Theoretical Calculations, and Reactivity Studies", J. Am. Chem. Soc., vol. 121, No. 28, 1999, pp. 6668-6682.

Delpech et al., "Ruthenium-Catalyzed Silylation of Ethylene by Disilanes", Organometallics, vol. 19, 2000, pp. 5750-5757.

Demonceau et al., "Cyclopropanation of Activated Olefins Catalysed by Ru-Phosphine Complexes", Tetrahedron Letters, vol. 36, No. 20, 1995, pp. 3519-3522.

Dioumaev et al., "Structure and Reactivity of Bis(silyl) Dihydride Complexes (PMe$_3$)$_3$Ru(SiR$_3$)$_2$(H)$_2$: Model Compounds and Real Intermediates in a Dehydrogenative C—Si Bond Forming Reaction", Journal of the American Chemical Society, vol. 125, 2003, pp. 8936-8948.

Djurovich et al., "Synthesis, Structure, and C—H Bond Activation Chemistry of ($\eta^6$arene)Ru(H)$_2$(SiMe$_3$)$_2$ Complexes", Organometallics, vol. 13, 1994, pp. 2551-2553.

Hashimoto et at., "Synthesis and Properties of a Silyl(silylene)ruthenium Complex: Activation Barrier of the Ru=Si Bond Rotation and Facile Replacement of the Methyl Groups with Alkoxy Groups of a Silyl Ligand", Organometallics, vol. 28, No. 14, 2009, pp. 3963-3965.

Hill et al., "Bis(methimazolyl)silyl Complexes of Ruthenium", Organometallics, vol. 29, No. 4, 2010, pp. 1026-1031.

Hossain et al., "Endohedral and Exohedral Complexes of T$_8$-Polyhedral Oligomeric Silsesquioxane (POSS) with Transition Metal Atoms and Ions", J. Phys. Chem. C, vol. 112, No. 41, 2008, pp. 16070-16077.

International Search Report (PCT/ISA/210) issued in PCT/JP2015/056200, dated May 26, 2015.

Lachaize et al., "Mechanistic studies on ethylene silylation with chlorosilanes catalysed by ruthenium complexes", Chem. Commun., 2003, pp. 214-215.

Matsubara et al., "A Triruthenium Carbonyl Cluster Bearing a Bridging Acenaphthylene Ligand: An Efficient Catalyst for Reduction of Esters, Carboxylic Acids, and Amides by Trialkylsilanes", J. Org. Chem., vol. 67, No. 14, 2002, pp. 4985-4988.

Miyamoto et al., "Selective Reduction of Carboxylic Acids to Aldehydes by a Ruthenium-catalyzed Reaction with 1,2-Bis(dimethylsilyl)benzene", Chem. Lett., vol. 41, 2012, pp. 229-231.

Montiel-Palma et al., "Agostic Si—H bond coordination assists C—H bond activation at ruthenium in bis(phosphinobenzylsilane) complexes", Chem. Commun., No. 38, Oct. 14, 2007, pp. 3963-3965.

Montiel-Palma et al., "Phosphinodi(benzylsilane) PhP{(o-C$_6$H$_4$CH$_2$)SiMe$_2$H}$_2$: A Versatile "PSi$_2$H$_x$" Pincer-Type Ligand at Ruthenium", Inorganic Chemistry, vol. 52, 2013, pp. 9798-9806.

Motoyama et al., "Self-Encapsulation of Homogeneous Catalyst Species into Polymer Gel Leading to a Facile and Efficient Separation System of Amine Products in the Ru-Catalyzed Reduction of Carboxamides with Polymethylhydrosiloxane (PMHS)", J. Am. Chem. Soc., vol. 127, No. 38, 2005, pp. 13150-13151.

Okazaki et al., "[Ru(xantsil)(CO)($\eta^6$-toluene)]: Synthon for a Highly Unsaturated Ruthenium(II) Complex through Facile Dissociation of the Toluene Ligand [xantsil = (9,9-dimethylxanthene-4,5-diyl)bis(dimethylsilyl)]", Organometallics, vol. 27, No. 5, 2008, pp. 918-926.

Pomeroy et al., "Preparation and Derivatives of cis-M(CO)$_4$(SiCl$_3$)$_2$ (M=Fe, Ru, Os)", Inorganic Chemistry, vol. 19, No. 12, 1980, pp. 3729-3735.

Sasakuma et al., "Functional group-selective poisoning of molecular catalysts: a ruthenium cluster-catalysed highly amide-selective silane reduction that does not affect ketones or esters", Chem. Commun., 2007, pp. 4916-4918.

Smart et al., "Step-by-Step Introduction of Silazane Moieties at Ruthenium: Different Extents of Ru—H—Si Bond Activation", Inorganic Chemistry, vol. 52, 2013, pp. 2654-2661.

Sunada et al., "Disilametallacycles as a Platform for Stabilizing M(II) and M(IV) (M=Fe, Ru) Centers: Synthesis and Characterization of Half-Sandwich Complexes and Their Application to Catalytic Double Silylation of Alkenes and Alkynes", Organometallics, vol. 32, 2013, pp. 2112-2120.

Süss-Fink et al., "The Cluster Anion [HRu$_3$(CO)$_{11}$]—as Catalyst in Hydroformylation, Hydrogenation, Silacarbonylation and Hydrosilylation Reactions of Ethylene and Propylene", Journal of Molecular Catalysis, vol. 16, 1982, pp. 231-242.

Svoboda et al., "Reactions of [(C$_6$H$_5$)$_3$P]$_3$RuCl$_2$ With Some Silicon Hydrides", Collect. Czech. Chem. Commun., vol. 39, 1974, pp. 1324-1329.

Takaoka et al., "E—H Bond Activation Reactions (E=H, C, Si, Ge) at Ruthenium: Terminal Phosphides, Silylenes, and Germylenes", Organometallics, vol. 28, No. 13, 2009, pp. 3744-3753.

Wada et al., "Intramolecular Aromatic C—H Bond Activation by a Silylene Ligand in a Methoxy-Bridged Bis(silylene)-Ruthenium Complex", Organometallics, vol. 16, No. 18, 1997, pp. 3870-3872.

Written Opinion (PCT/ISA/237) issued in PCT/JP2015/056200, dated May 26, 2015.

* cited by examiner

MONONUCLEAR RUTHENIUM COMPLEX AND ORGANIC SYNTHESIS REACTION USING SAME

TECHNICAL FIELD

This invention relates to mononuclear ruthenium complexes having ruthenium-silicon bonds. More specifically, the invention relates to mononuclear ruthenium complexes having catalytic activities in at least one of the following types of industrially useful reactions: hydrosilylation reactions, hydrogenation reactions, and carbonyl compound reduction reactions.

BACKGROUND ART

Hydrosilylation reactions, which entail the addition reaction of a Si—H functional compound with a compound having a carbon-carbon double bond or triple bond, are a useful means for synthesizing organosilicon compounds, and are synthesis reactions of industrial importance as well.

Platinum (Pt), palladium (Pd), and rhodium (Rh) compounds are known as catalysts for such hydrosilylation reactions. Of these, platinum compounds typified by Speier's catalyst and Karstedt's catalyst are most often used.

One problem with reactions in which platinum compounds are used as the catalyst is that, when adding a compound having Si—H functionality to a terminal olefin, internal rearrangement of the olefin arises as a secondary reaction. In such a system, because the catalyst does not exhibit addition reactivity with respect to internal olefins, unreacted olefin remains behind within the addition product. Therefore, in order to bring the reaction to completion, excess olefin which makes allowance for the portion that will be left behind due to secondary reactions must be used.

Another drawback is that, depending on the type of the olefin, selectivity of the α-adduct to the β-adduct worsens.

The largest problem is that the central metals Pt, Pd and Rh are all highly expensive noble metal elements. Numerous studies are being carried out in search of metal compound catalysts that are less expensive to use. In particular, although ruthenium (Ru) belongs to the noble metals, because it is a metal available at relatively low cost, there is a desire that it functions as a substitute for Pt, Pd and Rh.

In this connection, ruthenium compounds which have an $\eta^6$-arene group and in which organopolysiloxane is bonded, or vinylsiloxane is coordinated, to a Ru metal center have been reported (Patent Document 1). Although these compounds have been shown to be effective in an addition reaction between methylhydrogenpolysiloxane and methylvinylpolysiloxane, the yield is low in a reaction at 120° C.; to obtain a high yield, reaction must be carried out at an elevated temperature of 160° C.

A number of patents relating to Ru catalysts are cited in Patent Document 1 as prior-art literature (Patent Documents 2 to 6), but none of these catalysts appear superior to noble metal element-based catalysts in terms of reactivity, selectivity or cost-effectiveness.

Olefin hydrogenation reactions are also industrially important reactions. Noble metals such as Pt, Pd and Rh are used in conventional catalysts for such reactions, and the use of ruthenium, which is inexpensive among the noble metals, is desired. For example, some such reactions have used trinuclear ruthenium complexes of the sort shown in Non-Patent Document 1, but further improvement is desired in terms of reaction temperature, yield and the like.

Non-Patent Document 2 discloses mononuclear ruthenium complexes that are effective in hydrogenation reactions on tetrasubstituted olefins, which are regarded as having a low reaction yield, but the turnover number is low and high-pressure reaction conditions are required.

Methods for reducing carbonyl compounds include methods that use an aluminum or boron hydride compound or use hydrogen in the presence of a noble metal catalyst. Of carbonyl compounds, with regard to the reduction of ketones and aldehydes, hydride reactants and noble metal catalysts for hydrogenation which can induce the reaction to proceed under mild conditions and are stable and easy to handle are known. However, to reduce carboxylic acid derivatives such as esters and amides, use is primarily made of methods that employ powerful reducing agents such as lithium aluminum hydride or borane (Non-Patent Document 3). Unfortunately, these reducing agents are ignitable, water-prohibitive substances, and thus difficult to handle. Moreover, even when removing the aluminum or boron compound from the target product following the reaction, care is needed in handling. In addition, high-temperature, high-pressure hydrogen is needed to reduce carboxylic acid derivatives.

Although numerous methods for the use of hydrosilane compounds and methylhydrogenpolysiloxanes, which are stable in air and easy to handle, as reducing agents have been reported, such reactions require the addition of a strong acid or Lewis acid and an expensive noble metal catalyst. Recently, carbonyl compound reduction reactions that use relatively inexpensive ruthenium as the catalyst have been reported. Some of these reports even mention examples of use in amide-reducing reactions that, in conventional methods, require harsh conditions. Examples of specific ruthenium catalysts are mentioned in Non-Patent Documents 4 to 7, although high-activity catalysts which exhibit a higher turnover number are desired.

The following mononuclear complex compounds having σ bonds between ruthenium and silicon are known: divalent complexes having six-electron ligands (Non-Patent Documents 8 and 9), tetravalent complexes having two-electron ligands (Non-Patent Documents 10 and 11), tetravalent complexes having six-electron ligands (Non-Patent Documents 9 and 12), divalent complexes having thiourea groups on silicon (Non-Patent Document 13), divalent complexes having halogens on silicon (Non-Patent Document 14), anion complexes (Non-Patent Document 15), and divalent complexes having agostic Si—H ligands as two-electron ligands (Non-Patent Documents 15 and 16).

Divalent complexes which have no σ bonds between ruthenium and silicon and which have agostic Si—H ligands as two-electron ligands are also known (Non-Patent Documents 16 and 17).

In addition, the following mononuclear complex compounds having isonitrile as two-electron ligands are known: divalent complexes which have two σ bonds between ruthenium and silicon, have CO and also have halogen groups on silicon (Non-Patent Document 18), divalent complexes which both have two σ bonds between ruthenium and silicon and also have CO (Non-Patent Document 19), divalent complexes which have one σ bond between ruthenium and silicon and also have CO (Non-Patent Document 20), divalent complexes which have two σ bonds between ruthenium and silicon and also have halogen groups on silicon (Non-Patent Document 21), divalent complexes which have only one σ bond between ruthenium and silicon (Non-Patent Document 22), and divalent complexes which have no σ bonds between ruthenium and silicon (Non-Patent Document 17).

However, above Non-Patent Documents 8 to 22 do not in any way suggest the possibility that the ruthenium complexes disclosed therein have catalytic activities in hydrosilylation reactions, olefin hydrogenation reactions and/or carbonyl compound reduction reactions.

As for examples of reactions in which a ruthenium complex is used as a catalyst, an addition reaction between ethylene and dimethylchlorosilane (Non-Patent Document 23) has been reported, but the reactivity and selectivity of this reaction is low.

Examples of addition reactions between disilane and ethylene (Non-Patent Document 24) have been reported, and a disilametallacycle structure as the intermediate has been proposed as the putative reaction mechanism. However, a ligand-containing complex structure has not been elucidated, and no identification has been made suggesting a dimetallacycle structure. The example reactions reported here also have a poor reactivity and selectivity, and cannot be regarded as complexes exhibiting adequate catalytic activity. Furthermore, the chief product of this reaction mechanism is vinylsilane or cyclic silane due to dehydrogenative silylation; only a trace amount of addition product is present.

PRIOR ART DOCUMENTS

Patent Documents

Patent Document 1: JP No. 5032561
Patent Document 2: U.S. Patent Application No. 2004/0092759
Patent Document 3: U.S. Pat. No. 5,559,264
Patent Document 4: EP-A 0403706
Patent Document 5: U.S. Pat. No. 5,248,802
Patent Document 6: West German Patent Application No. 2810032

Non-Patent Documents

Non-Patent Document 1: G. Suss-Fink, et al., *J. Mol. Cat.*, 1982, 16, 231
Non-Patent Document 2: C. H. Lau, et al., *Organometallics*, 1997, 16, 34
Non-Patent Document 3: W. R. Brown, *Organic Reactions*, 1941, 6, 470
Non-Patent Document 4: K. Miyamoto, et al., *Chem. Lett.*, 2012, 229
Non-Patent Document 5: K. Matsubara, et al., *J. Org. Chem.*, 2002, 67, 4985
Non-Patent Document 6: Y. Motoyama, et al., *J. Am. Chem. Soc.*, 2005, 127, 13150
Non-Patent Document 7: H. Sasakuma, et al., *Chem. Commun.*, 2007, 4916
Non-Patent Document 8: F. R. Lemke, et al., *Organometallics*, 2003, 22, 4928
Non-Patent Document 9: H. Nagashima, et al., *Organometallics*, 2013, 32, 2112
Non-Patent Document 10: S. Sabo-Etienne, et al., *Inorg. Chem.*, 2013, 52, 2654
Non-Patent Document 11: D. H. Berry, et al., *J. Am. Chem. Soc.*, 2003, 125, 8936
Non-Patent Document 12: D. H. Berry, et al., *Organometallics*, 1994, 13, 2551
Non-Patent Document 13: A. F. Hill, et al., *Organometallics*, 2010, 29, 1026
Non-Patent Document 14: P. Svoboda, et al., *Collection of Czechosiovak Chemical Communication*, 1974, 39, 1324
Non-Patent Document 15: J. C. Peters, et al., *Organometallics*, 2009, 28, 3744
Non-Patent Document 16: S. Sabo-Etienne, et al., *Inorg. Chem.*, 2013, 52, 9798
Non-Patent Document 17: S. Sabo-Etienne, et al., *J. Am. Chem. Soc.*, 1999, 121,
Non-Patent Document 18: P. K. Pomeroy, et al., *Inorg. Chem.*, 1980, 19, 3729
Non-Patent Document 19: H. Tobita, et al., *Organometallics*, 2008, 27, 918
Non-Patent Document 20: H. Tobita, et al., *Organometallics*, 2009, 28, 3963
Non-Patent Document 21: N. J. Cooper, et al., *Angew. Chem. Int. Ed. Engl.*, 1992, 32, 83
Non-Patent Document 22: H. Tobita, et al., *Organometallics*, 1997, 16, 3870
Non-Patent Document 23: S. Lachaize, et al., *Chem. Commun.*, 2003, 314
Non-Patent Document 24: F. Delpech, et al., *Organometallics*, 2000, 19, 5750

SUMMARY OF THE INVENTION

Problems to be Solved by the Invention

It is therefore an object of this invention to provide a mononuclear ruthenium complex having ruthenium-silicon bonds which is capable of exhibiting an excellent catalytic activity in at least one of the following three types of reactions: hydrosilylation reactions, hydrogenation reactions and carbonyl compound reduction reactions. Another object of the invention is to provide methods for carrying out the respective reactions under mild conditions using this complex.

Means for Solving the Problems

The inventors have conducted extensive investigations, as a result of which they have discovered that certain neutral or cationic mononuclear divalent ruthenium complexes having ruthenium-silicon bonds are able to exhibit an excellent catalytic activity in at least one of the following types of reactions: hydrosilylation reactions, hydrogenation reactions and carbonyl compound reduction reactions, and that, using such complexes, the respective reactions proceed under mild conditions.

Accordingly, the invention provides:
1. A neutral or cationic mononuclear divalent ruthenium complex which is characterized by having formula (1)

[Chemical Formula 1]

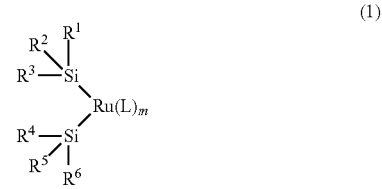

(wherein $R^1$ to $R^6$ are each independently a hydrogen atom or an alkyl, aryl, aralkyl, organooxy, monoorganoamino, diorganoamino, monoorganophosphino, diorganophosphino, monoorganosilyl, diorganosilyl, triorganosilyl or organothio group which may be substituted with X, or at least one pair of any of $R^1$ to $R^3$ and any of $R^4$ to $R^6$, taken together, represent a crosslinking substituent, X is a halogen atom, an organooxy group, a monoorganoamino group, a diorganoamino group or an organothio group; each L is independently a two-electron ligand other than CO and thiourea ligands, and two L's may be bonded to one another; and m is the integer 3 or 4);

2. The neutral or cationic mononuclear divalent ruthenium complex of 1 above, wherein L is at least one type of two-electron ligands selected from the group consisting of molecular hydrogen, amines, imines, nitrogen-containing heterocycles, phosphines, phosphites, arsines, alcohols, thiols, ethers, sulfides, nitriles, isonitriles, aldehydes, ketones, alkenes of 2 to 30 carbon atoms, alkynes of 2 to 30 carbon atoms and triorganohydrosilanes;

3. The neutral or cationic mononuclear divalent ruthenium complex of 1 above which has formula (2)

[Chemical Formula 2]

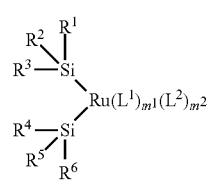

(2)

(wherein $R^1$ to $R^6$ are as defined above; $L^1$ is at least one type of two-electron ligands selected from among isonitriles, amines, imines, nitrogen-containing heterocycles, phosphines, phosphites and sulfides, with the proviso that when a plurality of $L^1$ ligands are present, two $L^1$ ligands may be bonded to one another; $L^2$ is a two-electron ligand other than CO, thiourea and $L^1$ ligands, with the proviso that when a plurality of $L^2$ ligands are present, two $L^2$ ligands may be bonded to one another; and $m^1$ is an integer from 1 to 4, $m^2$ is an integer from 0 to 3, and $m^1+m^2$ is 3 or 4);

4. The neutral or cationic mononuclear divalent ruthenium complex of 3 above, wherein $L^1$ is at least one type of two-electron ligands selected from the group consisting of isonitriles, nitrogen-containing heterocycles and phosphites (with the proviso that when a plurality of $L^1$ ligands are present, two $L^1$ ligands may be bonded to one another);

5. The neutral or cationic mononuclear divalent ruthenium complex of 3 or 4 above, wherein $L^2$ is a triorganohydrosilane (with the proviso that when a plurality of $L^2$ ligands are present, two $L^2$ ligands may be bonded to one another);

6. The neutral or cationic mononuclear divalent ruthenium complex of any one of 3 to 5 above, wherein $m^1$ and $m^2$ are both 2;

7. The neutral or cationic mononuclear divalent ruthenium complex of 6 above, wherein $R^1$ to $R^6$ are each independently an alkyl, aryl or aralkyl group that may be substituted with X, which is as defined above, and the $L^2$ ligands are triorganohydrosilanes of the formulas $H-SiR^7R^8R^9$ and $H-SiR^{10}R^{11}R^{12}$ (wherein $R^7$ to $R^{12}$ are each independently an alkyl, aryl or aralkyl group that may be substituted with X, which is as defined above); at least one pair of any of $R^1$ to $R^3$ and any of $R^4$ to $R^6$ or any of $R^7$ to $R^9$, or at least one pair of any of $R^{10}$ to $R^{12}$ and any of $R^4$ to $R^6$ or any of $R^7$ to $R^9$, may bond together to form a crosslinking substituent; or at least one pair of any of $R^1$ to $R^3$ and any of $R^4$ to $R^6$ or any of $R^7$ to $R^9$ may bond together to form a crosslinking substituent, and at least one pair of any of $R^{10}$ to $R^{12}$ and any of $R^4$ to $R^6$ or any of $R^7$ to $R^9$ may bond together to form a crosslinking substituent;

8. The neutral or cationic mononuclear divalent ruthenium complex of any one of 1 to 7 above, wherein any one of $R^1$ to $R^3$ and any one of $R^4$ to $R^6$ bond together to form a crosslinking substituent;

9. The neutral or cationic mononuclear divalent ruthenium complex of 7 above, wherein any one of $R^1$ to $R^3$ and any one of $R^4$ to $R^6$ or any one of $R^7$ to $R^9$ bond together to form a first crosslinking substituent, and any one of $R^{10}$ to $R^{12}$ bonds together with, among any one of $R^4$ to $R^6$ and any one of $R^7$ to $R^9$, a substituent on Si that does not take part in formation of the first crosslinking substituent to form a second crosslinking substituent;

10. The neutral or cationic mononuclear divalent ruthenium complex of 9 above, wherein any one of $R^1$ to $R^3$ bonds together with any one of $R^4$ to $R^6$ to form an o-phenylene group which may be substituted with Y (Y being a hydrogen atom, a halogen atom, an alkyl group of 1 to 10 carbon atoms or an alkoxy group of 1 to 10 carbon atoms, with the proviso that when a plurality of Y's are present, they may be the same or different), and any one of $R^{10}$ to $R^{12}$ bonds together with any one of $R^7$ to $R^9$ to form an o-phenylene group which may be substituted with Y (wherein Y is as defined above);

11. A catalyst which comprises the neutral or cationic mononuclear divalent ruthenium complex of any one of 1 to 10 above and has activity in at least one reaction selected from the group consisting of hydrosilylation reactions, hydrogenation reactions and carbonyl compound reduction reactions;

12. A method for preparing an addition compound, characterized by comprising the step of hydrosilylating an aliphatic unsaturated bond-containing compound with a Si—H bond-containing hydrosilane or organohydropolysiloxane in the presence of the catalyst of 11 above;

13. A method for preparing an alkane compound, characterized by comprising the step of hydrogenating a compound having an aliphatic unsaturated bond in the presence of the catalyst of 11 above;

14. A method for preparing an amine compound, characterized by comprising the step of reducing an amide compound with a Si—H bond-containing silane or organohydropolysiloxane in the presence of the catalyst of 11 above; and 15. A method for preparing an alcohol compound, characterized by comprising the step of reducing an aldehyde compound, ketone compound or ester compound with a Si—H bond-containing silane or organohydropolysiloxane in the presence of the catalyst of 11 above.

Advantageous Effects of the Invention

When the hydrosilylation of an aliphatic unsaturated group-containing compound with a Si—H bond-containing silane or a polysiloxane is carried out using a mononuclear ruthenium complex of the invention as the catalyst, an addition reaction under conditions from room temperature up to 100° C. becomes possible. In particular, addition reactions with industrially useful polysiloxanes, and also trialkoxysilanes and dialkoxysilanes, proceed effectively. Mention is often made in the literature that reactions which form unsaturated group-containing compounds by dehydrogenative silylation take place preferentially to addition reactions to unsaturated groups. However, using the inventive catalysts, addition reactions to unsaturated groups preferentially proceed.

The hydrogenation reaction can be carried out under mild conditions of room temperature and a hydrogen gas pressure of 1 atmosphere, and is effective as well for hydrogenating polysubstituted alkenes, which has been difficult with conventional methods. Also, the catalyst has tolerance to temperature and pressure, and exhibits activity even under heated or pressurized conditions of 80° C. or 10 atmospheres.

In the carbonyl compound reduction reaction, the desired reduced compound can be obtained by reacting an amide compound, aldehyde compound, ketone compound or ester compound with a Si—H group-containing silane or a polysiloxane that is easy to handle.

BRIEF DESCRIPTION OF THE DIAGRAMS

Figure 2:
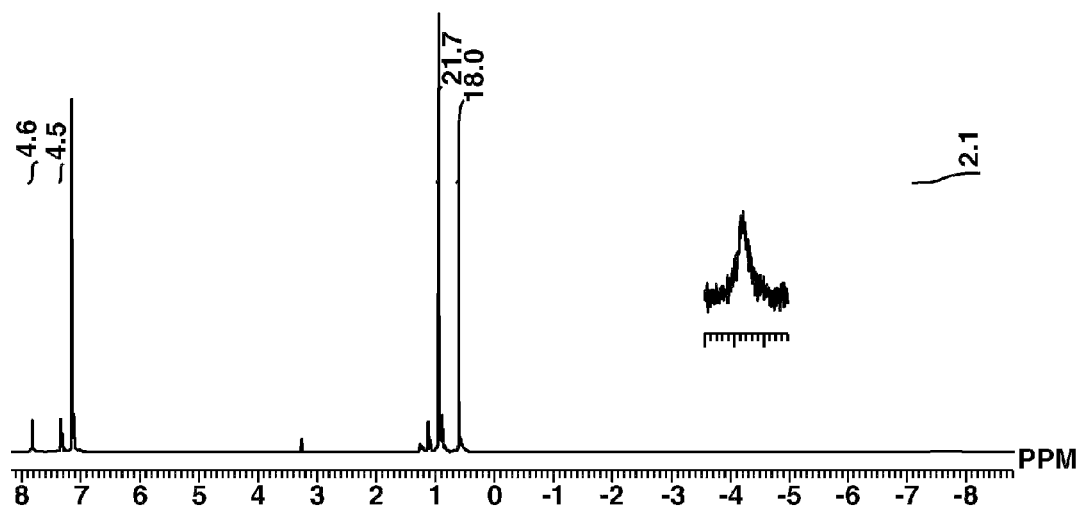
Figure 3:
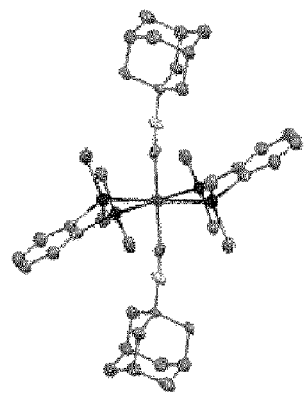
Figure 4:
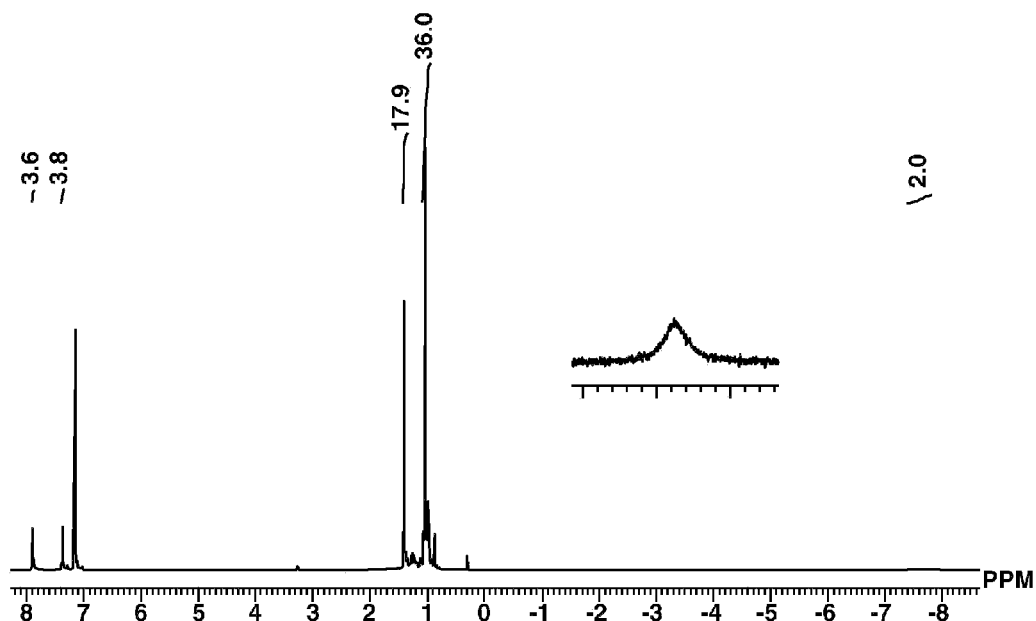
Figure 5:
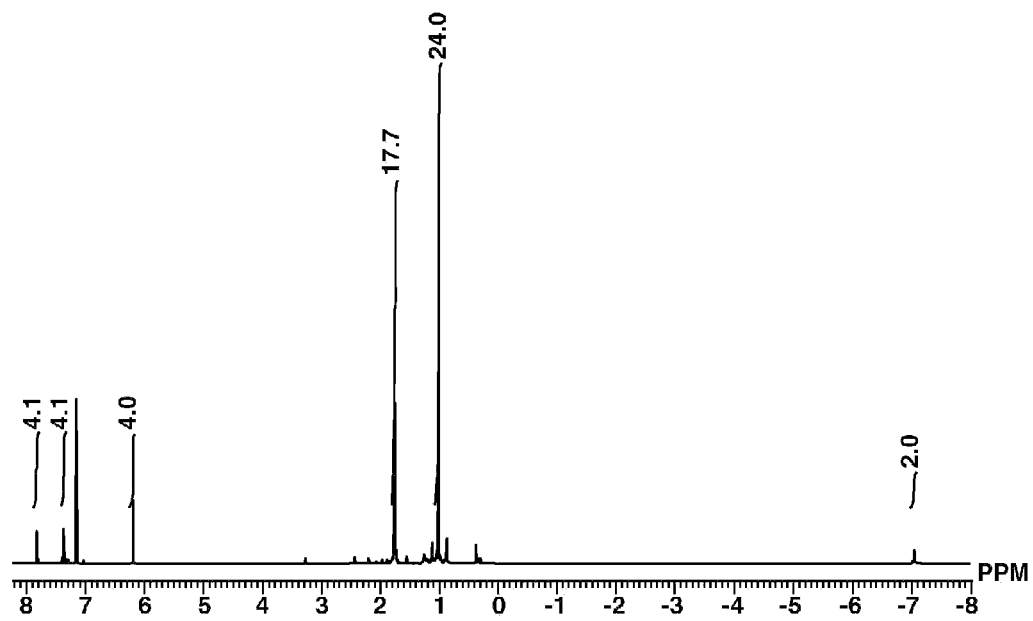
Figure 6:
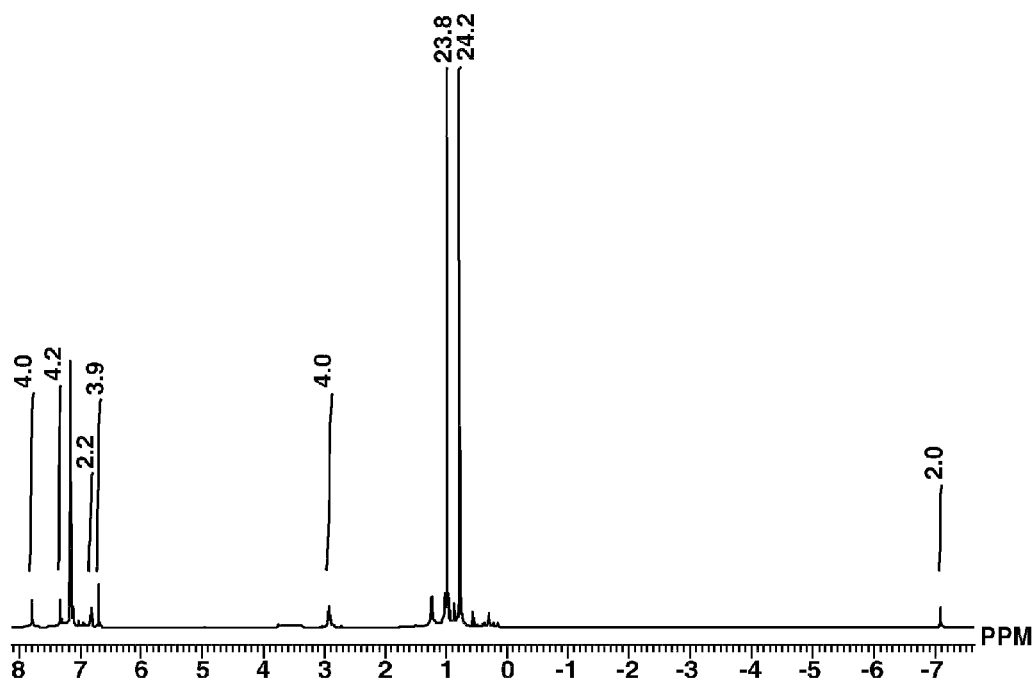
Figure 7:
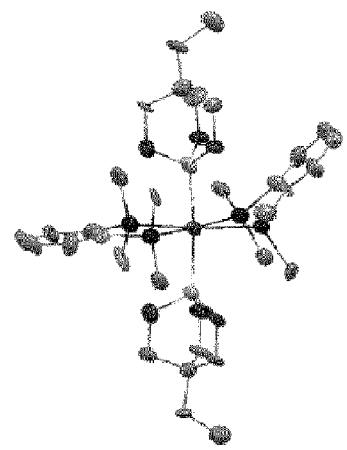
Figure 8:
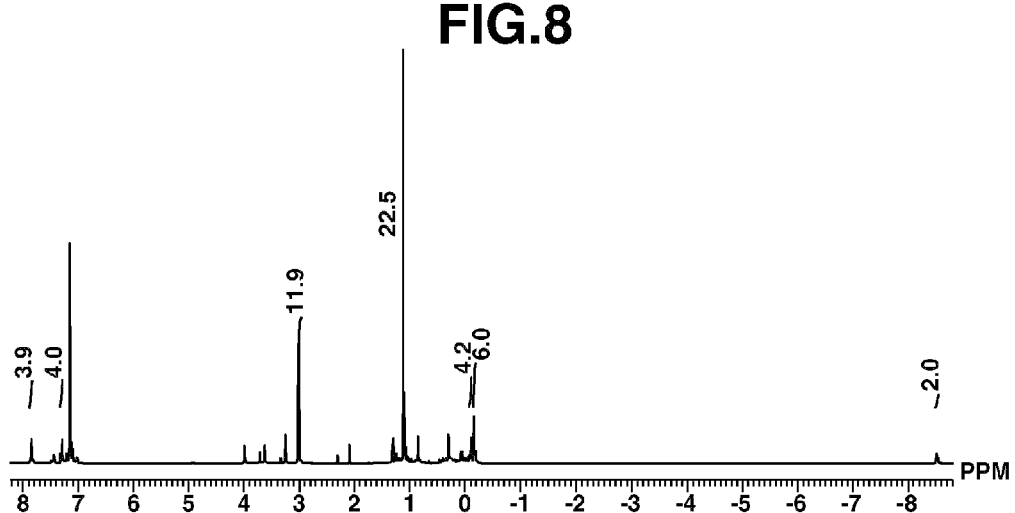
Figure 9:
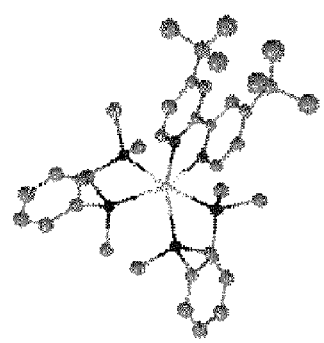
Figure 10:
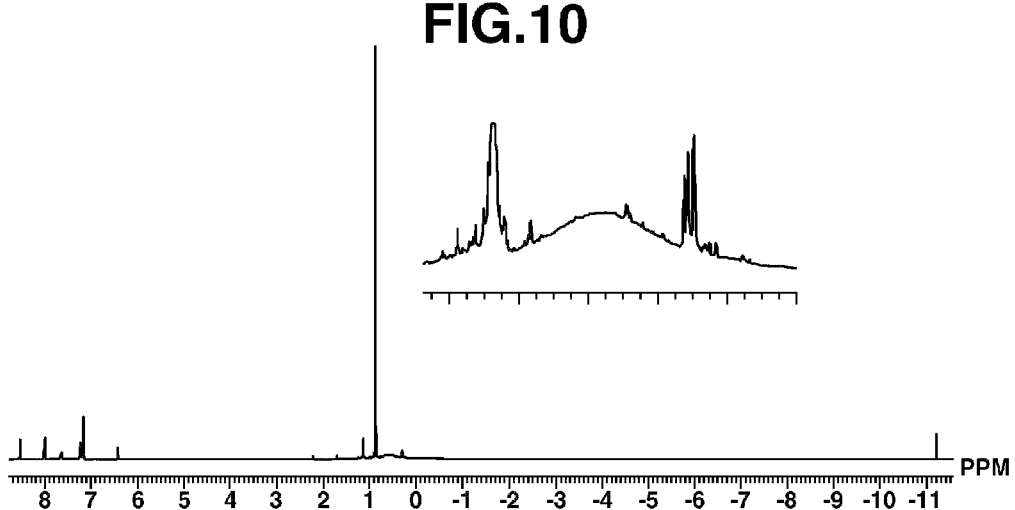

FIG. 1 is a diagram showing the structure of Ruthenium Complex A obtained in Working Example 1.
FIG. 2 is an $^1$H-NMR spectrum of Ruthenium Complex A obtained in Working Example 1.
FIG. 3 is a diagram showing the structure of Ruthenium Complex B obtained in Working Example 2.
FIG. 4 is an $^1$H-NMR spectrum of Ruthenium Complex B obtained in Working Example 2.
FIG. 5 is an $^1$H-NMR spectrum of Ruthenium Complex C obtained in Working Example 3.
FIG. 6 is an $^1$H-NMR spectrum of Ruthenium Complex D obtained in Working Example 4.
FIG. 7 is a diagram showing the structure of Ruthenium Complex E obtained in Working Example 5.
FIG. 8 is an $^1$H-NMR spectrum of Ruthenium Complex E obtained in Working Example 5.
FIG. 9 is a diagram showing the structure of Ruthenium Complex F obtained in Working Example 6.
FIG. 10 is an $^1$H-NMR spectrum of Ruthenium Complex F obtained in Working Example 6.

EMBODIMENT FOR CARRYING OUT THE INVENTION

The invention is described more fully below.
As shown in formula (1), the mononuclear ruthenium complex of the invention is a neutral or cationic divalent complex which has two Ru—Si bonds and in which three or four two-electron ligands other than carbon monoxide (CO) and thiourea ligands are coordinated to ruthenium.

[Chemical Formula 3]

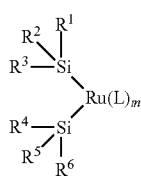

(1)

In formula (1), $R^1$ to $R^6$ are each independently a hydrogen atom or an alkyl, aryl, aralkyl, organooxy, monoorganoamino, diorganoamino, monoorganophosphino, diorganophosphino, monoorganosilyl, diorganosilyl, triorganosilyl or organothio group which may be substituted with X, or at least one pair of any of $R^1$ to $R^3$ with any of $R^4$ to $R^6$, taken together, represent a crosslinking substituent; and X is a halogen atom, an organooxy group, a monoorganoamino group, a diorganoamino group or an organothio group.

The alkyl group may be linear, branched or cyclic and has a number of carbon atoms which, although not particularly limited, is preferably from 1 to 30, and more preferably from 1 to 10. Illustrative examples include linear or branched alkyl groups such as methyl, ethyl, n-propyl, isopropyl, n-butyl, isobutyl, s-butyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl and n-eicosanyl groups; and cycloalkyl groups such as cyclopropyl, cyclobutyl, cyclopentyl, cyclohexyl, cycloheptyl, cyclooctyl and cyclononyl groups.

The aryl group has a number of carbon atoms which, although not particularly limited, is preferably from 6 to 30, and more preferably from 6 to 20. Illustrative examples include phenyl, 1-naphthyl, 2-naphthyl, anthryl, phenanthryl, o-biphenylyl, m-biphenylyl and p-biphenylyl groups.

The aralkyl group has a number of carbon atoms which, although not particularly limited, is preferably from 7 to 30, and more preferably from 7 to 20. Illustrative examples include benzyl, phenylethyl, phenylpropyl, naphthylmethyl, naphthylethyl and naphthylpropyl groups.

Examples of the organooxy group include, without particular limitation, alkoxy, aryloxy and aralkyloxy groups of the formula RO (wherein R is a substituted or unsubstituted alkyl group of 1 to 30 carbon atoms, aryl group of 6 to 30 carbon atoms or aralkyl group of 7 to 30 carbon atoms).

The alkoxy group has a number of carbon atoms which, although not particularly limited, is preferably from 1 to 30, and especially from 1 to 10. Illustrative examples include methoxy, ethoxy, n-propoxy, i-propoxy, c-propoxy, n-butoxy, i-butoxy, s-butoxy, t-butoxy, n-pentoxy, n-hexoxy, n-heptyloxy, n-octyloxy, n-nonyloxy and n-decyloxy groups.

The aryloxy group has a number of carbon atoms which, although not particularly limited, is preferably from 6 to 30, and especially from 6 to 20. Illustrative examples include phenoxy, 1-naphthyloxy, 2-naphthyloxy, anthryloxy and phenanthryloxy groups.

The aralkyloxy group has a number of carbon atoms which, although not particularly limited, is preferably from 7 to 30, and especially from 7 to 20. Illustrative examples include benzyloxy, phenylethyloxy, phenylpropyloxy, 1- or 2-naphthylmethyloxy, 1- or 2-naphthylethyloxy and 1- or 2-naphthylpropyloxy groups.

The organothio group is exemplified by the above organooxy groups in which the oxygen atom is substituted with a sulfur atom.

The monoorganoamino group, although not particularly limited, is preferably one of the formula $RNH_2$ (wherein R is as defined above), the preferred number of carbon atoms on R being the same as for the above-described alkoxy, aryloxy and aralkyloxy groups. Illustrative examples include linear or branched monoalkylamino groups such as methylamino, ethylamino, n-propylamino, isopropylamino, n-butylamino, isobutylamino, s-butylamino, t-butylamino, n-pentylamino, n-hexylamino, n-heptylamino, n-octylamino, n-nonylamino, n-decylamino, n-undecylamino, n-dodecylamino, n-tridecylamino, n-tetradecylamino, n-pentadecylamino, n-hexadecylamino, n-heptadecylamino, n-octadecylamino, n-nonadecylamino and n-eicosanylamino groups; monocycloalkylamino groups such as cyclopropylamino, cyclobutylamino, cyclopentylamino, cyclohexylamino, cycloheptylamino, cyclooctylamino and cyclononylamino groups; monoarylamino groups such as anilino and 1- or 2-naphthylamino groups; and monoaralkylamino groups such as benzylamino, phenylethylamino, phenylpropylamino and 1- or 2-naphthylmethylamino groups.

The diorganoamino group, although not particularly limited, is preferably one of the formula $R_2NH$ (wherein each R is independently as defined above), the preferred number of carbon atoms on R being the same as for the above-described alkoxy, aryloxy and aralkyloxy groups. Illustrative examples include linear or branched dialkylamino groups such as dimethylamino, diethylamino, di-n-propylamino, diisopropylamino, di-n-butylamino, diisobutylamino, di-s-butylamino, di-t-butylamino, di-n-pentylamino, di-n-hexylamino, di-n-heptylamino, di-n-octylamino, di-n-nonylamino, di-n-decylamino, di-n-undecylamino, di-n-dodecylamino, di-n-tridecylamino, di-n-tetradecylamino, di-n-pentadecylamino, di-n-hexadecylamino, di-n-heptadecylamino, di-n-octadecylamino, di-n-nonadecylamino, di-n-eicosanylamino, N-ethylmethylamino, N-isopropylmethylamino and N-butylmethylamino groups; dicycloalkylamino groups such as dicyclopropylamino, dicyclobutylamino, dicyclopentylamino, dicyclohexylamino, dicycloheptylamino, dicyclooctylamino, dicyclononylamino and cyclopentylcyclohexylamino groups; alkylarylamino groups such as N-methylanilino, N-ethylanilino and N-n-propylanilino groups; diarylamino groups such as diphenylamino, 4,4'-bisnaphthylamino and N-phenyl-1- or 2-naphthylamino groups; and diaralkylamino groups such as dibenzylamino, bis(phenylethyl)amino, bis(phenylpropyl)amino and bis(1- or 2-naphthylmethyl)amino groups.

The monoorganophosphino group, although not particularly limited, is preferably one of the formula RPH (wherein R is as defined above), the preferred number of carbon atoms on R being the same as for the above-described alkoxy, aryloxy and aralkyloxy groups. Illustrative examples include linear or branched monoalkylphosphino groups such as methylphosphino, ethylphosphino, n-propylphosphino, isopropylphosphino, n-butylphosphino, isobutylphosphino, s-butylphosphino, t-butylphosphino, n-pentylphosphino, n-hexylphosphino, n-heptylphosphino, n-octylphosphino, n-nonylphosphino, n-decylphosphino, n-undecylphosphino, n-dodecylphosphino, n-tridecylphosphino, n-tetradecylphosphino, n-pentadecylphosphino, n-hexadecylphosphino, n-heptadecylphosphino, n-octadecylphosphino, n-nonadecylphosphino and n-eicosanylphosphino groups; monocycloalkylphosphino groups such as cyclopropylphosphino, cyclobutylphosphino, cyclopentylphosphino, cyclohexylphosphino, cycloheptylphosphino, cyclooctylphosphino and cyclononylphosphino groups; monoarylphosphino groups such as phenylphosphino and 1- or 2-naphthylphosphino groups; and monoaralkylphosphino groups such as benzylphosphino groups.

The diorganophosphino group, although not particularly limited, is preferably one of the formula $R_2P$ (wherein each R is independently as defined above), the preferred number of carbon atoms on R being the same as for the above-described alkoxy, aryloxy and aralkyloxy groups. Illustrative examples include linear or branched dialkylphosphino groups such as dimethylphosphino, diethylphosphino, di-n-propylphosphino, diisopropylphosphino, di-n-butylphosphino, diisobutylphosphino, di-s-butylphosphino, di-t-butylphosphino, di-n-pentylphosphino, di-n-hexylphosphino, di-n-heptylphosphino, di-n-octylphosphino, di-n-nonylphosphino, di-n-decylphosphino, di-n-undecylphosphino, di-n-dodecylphosphino, di-n-tridecylphosphino, di-n-tetradecylphosphino, di-n-pentadecylphosphino, di-n-hexadecylphosphino, di-n-heptadecylphosphino, di-n-octadecylphosphino and di-n-eicosanylphosphino groups; dicycloalkylphosphino groups such as dicyclopropylphosphino, dicyclobutylphosphino, dicyclopentylphosphino, dicyclohexylphosphino, dicycloheptylphosphino, dicyclooctylphosphino and dicyclononylphosphino groups; alkylarylphosphino groups such as cyclohexylphenylphosphino groups; diarylphosphino groups such as diphenylphosphino and bis(1- or 2-naphthyl)phosphino groups; and diaralkylphosphino groups such as dibenzylphosphino, bis(phenylethyl)phosphino and bis(1- or 2-naphthylmethyl)phosphino groups.

The monoorganosilyl group, although not particularly limited, is preferably one of the formula $RSiH_2$ (wherein R is as defined above), the preferred number of carbon atoms on R being the same as for the above-described alkoxy, aryloxy and aralkyloxy groups. Illustrative examples include linear or branched monoalkylsilyl groups such as methylsilyl, ethylsilyl, n-propylsilyl, isopropylsilyl, n-butylsilyl, isobutylsilyl, s-butylsilyl, t-butylsilyl, n-pentylsilyl, n-hexylsilyl, n-heptylsilyl, n-octylsilyl, n-nonylsilyl, n-decylsilyl, n-undecylsilyl, n-dodecylsilyl, n-tridecylsilyl, n-tetradecylsilyl, n-pentadecylsilyl, n-hexadecylsilyl, n-heptadecylsilyl, n-octadecylsilyl, n-nonadecylsilyl and n-eicosanylsilyl groups; monocycloalkylsilyl groups such as cyclopropylsilyl, cyclobutylsilyl, cyclopentylsilyl, cyclohexylsilyl, cycloheptylsilyl, cyclooctylsilyl and cyclononylsilyl groups; monoarylsilyl groups such as phenylsilyl, and 1- or 2-naphthylsilyl groups; and monoaralkylsilyl groups such as benzylsilyl, phenylethylsilyl, phenylpropylsilyl, and 1- or 2-naphthylmethylsilyl groups.

The diorganosilyl group, although not particularly limited, is preferably one of the formula $R_2SiH$ (wherein each R is independently as defined above), the preferred number of carbon atoms on R being the same as for the above-described alkoxy, aryloxy and aralkyloxy groups. Illustrative examples include linear or branched dialkylsilyl groups such as dimethylsilyl, diethylsilyl, di-n-propylsilyl, diisopropylsilyl, di-n-butylsilyl, diisobutylsilyl, di-s-butylsilyl, di-t-butylsilyl, di-n-pentylsilyl, di-n-hexylsilyl, di-n-heptylsilyl, di-n-octylsilyl, di-n-nonylsilyl, d-n-decylsilyl, di-n-undecylsilyl, di-n-dodecylsilyl, di-n-tridecylsilyl, di-n-tetradecylsilyl, di-n-pentadecylsilyl, di-n-hexadecylsilyl, di-n-heptadecylsilyl, di-n-octadecylsilyl, di-n-nonadecylsilyl, di-n-eicosanylsilyl, ethylmethylsilyl, isopropylmethylsilyl and butylmethylsilyl groups; dicycloalkylsilyl groups such as dicyclopropylsilyl, dicyclobutylsilyl, dicyclopentylsilyl, dicyclohexylsilyl, dicycloheptylsilyl, dicyclooctylsilyl, dicyclononylsilyl and cyclopentylcyclohexylsilyl groups; alkylarylsilyl groups such as (meth)phenylsilyl, (ethyl)phenylsilyl and (n-propyl)phenylsilyl groups; diarylsilyl groups such as diphenylsilyl, bis(1- or 2-naphthyl)silyl and phenyl-1- or 2-naphthylsilyl groups; and diaralkylsilyl groups such as dibenzylsilyl, bis(phenylethyl)silyl, bis(phenylpropyl)silyl and bis(1- or 2-naphthylmethyl)silyl groups.

The triorganosilyl group, although not particularly limited, is preferably one of the formula $R_3Si$ (wherein each R is independently as defined above), the preferred number of carbon atoms on R being the same as for the above-described alkoxy, aryloxy and aralkyloxy groups. Illustrative examples include linear or branched trialkylsilyl groups such as trimethylsilyl, triethylsilyl, tri-n-propylsilyl, triisopropylsilyl, tri-n-butylsilyl, triisobutylsilyl, tri-s-butylsilyl, tri-t-butylsilyl, tri-n-pentylsilyl, tri-n-hexylsilyl, tri-n-heptylsilyl, tri-n-octylsilyl, tri-n-nonylsilyl, tri-n-decylsilyl, tri-n-undecylsilyl, tri-n-dodecylsilyl, tri-n-tridecylsilyl, tri-n-tetradecylsilyl, tri-n-pentadecylsilyl, tri-n-hexadecylsilyl, tri-n-heptadecylsilyl, tri-n-octadecylsilyl, tri-n-nonadecylsilyl, tri-n-eicosanylsilyl, ethyldimethylsilyl, diisopropylmethylsilyl and dibutylmethylsilyl groups; tricycloalkylsilyl groups such as tricyclopropylsilyl, tricyclobutylsilyl, tricyclopentylsilyl, tricyclohexylsilyl, tricycloheptylsilyl, tricyclooctylsilyl and tricyclononylsilyl groups; alkylarylsilyl groups such as (meth)diphenylsilyl, (ethyl)diphenylsilyl and (n-propyl)diphenylsilyl groups; triarylsilyl groups such as triphenylsilyl, tri(1- or 2-naphthyl)silyl and diphenyl-1- or 2-naphthylsilyl groups; and triaralkylsilyl groups such as tribenzylsilyl, tri(phenylethyl)silyl, tri(phenylpropyl)silyl and tri(1- or 2-naphthylmethyl)silyl groups.

In each of the above substituents, at least one hydrogen atom on R may be substituted with the substituent X. Examples of X include halogen atoms, organooxy groups, monoorganoamino groups, diorganoamino groups and organothio groups, the organooxy, monoorganoamino, diorganoamino and organothio groups being exemplified in the same way as above.

Examples of halogen atoms include fluorine, chlorine, bromine and iodine atoms, with fluorine atoms being preferred. Preferred fluorine-substituted alkyl groups include trifluoropropyl, nonafluorohexyl and heptadecylfluorodecyl groups.

Of the various above substituents, $R^1$ to $R^6$ are each independently an alkyl group of 1 to 30 carbon atoms, aryl group of 6 to 30 carbon atoms, aralkyl group of 7 to 30 carbon atoms, alkyl group of 1 to 10 carbon atoms or aryl group of 6 to 10 carbon atoms which may be substituted with X.

The crosslinking substituent where at least one pair of any of $R^1$ to $R^3$ and any of $R^4$ to $R^6$ are bonded together is not particularly limited, provided it is a substituent capable of crosslinking two silicon atoms. Illustrative examples include —O—, —S—, —NH—, —NR— (R being as defined above), —PR— (R being as defined above), —NH—(CH$_2$)$_k$—NH— (k being an integer from 1 to 10), —NR—(CH$_2$)$_k$—NR— (k being as defined above, and each R being independently as defined above), —PH—(CH$_2$)$_k$—PH— (k being as defined above), —PR—(CH$_2$)$_k$—PR— (k being as defined above, and each R being independently as defined above), —C≡C—, an alkylene group of 1 to 10 carbon atoms, an arylene group of 6 to 30 carbon atoms, an aralkylene group of 7 to 30 carbon atoms, —(CH$_2$O)$_k$— (k being as defined above), —(CH$_2$)$_k$—O—(CH$_2$)$_k$— (each k being independently as defined above), —O—(CH$_2$)$_k$—O— (k being as defined above), —R'—O—(CH$_2$)$_k$—O—R'— (each R' being independently an alkylene group of 1 to 10 carbon atoms, an arylene group of 6 to 30 carbon atoms or an aralkylene group of 7 to 30 carbon atoms, and k being as defined above), —(CH$_2$S)$_k$— (k being as defined above), —(CH$_2$)$_k$—S—(CH$_2$)$_k$— (each k being independently as defined above), —S—(CH$_2$)$_k$—S— (k being as defined above), —R'—S—(CH$_2$)$_k$—O—R'— (each R' being independently as defined above, and k being as defined above), —SiR$_2$— (each R being independently as defined above), —(CH$_2$)$_k$—SiR$_2$—(CH$_2$)$_k$— (each R being independently as defined above, and each k being independently as defined above).

Examples of the alkylene group of 1 to 10 carbon atoms include methylene, ethylene, propylene, trimethylene, tetramethylene, pentamethylene and hexamethylene.

Examples of arylene groups of 6 to 30 carbon atoms include o-phenylene (1,2-phenylene), 1,2-naphthylene, 1,8-naphthylene and 2,3-naphthylene.

Examples of aralkylene groups of 7 to 30 carbon atoms include —(CH$_2$)$_k$—Ar— (Ar being an arylene group of 6 to 20 carbon atoms, and k being as defined above), —Ar—(CH$_2$)$_k$— (Ar and k being as defined above) and —(CH$_2$)$_k$—Ar—(CH$_2$)$_k$— (Ar being as defined above, and each k being independently as defined above).

At least one hydrogen atom on the above alkylene, arylene and aralkylene groups may be substituted with the substituent X (X being as defined above).

Letting Z represent a crosslinking substituent, the number of Z's that connect two silicon atoms is from 1 to 3. Mononuclear ruthenium complexes having such crosslinking substituents Z are shown in the following formulas.

[Chemical Formula 4]

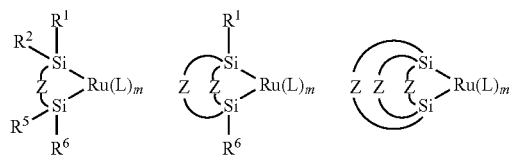

Here, $R^1$, $R^2$, $R^5$, $R^6$, L and m are as defined above, and Z is a crosslinking substituent.

Illustrative examples of disilametallacycle structures having crosslinking substituents include, but are not limited to, those shown in the following formulas.

[Chemical Formula 5]

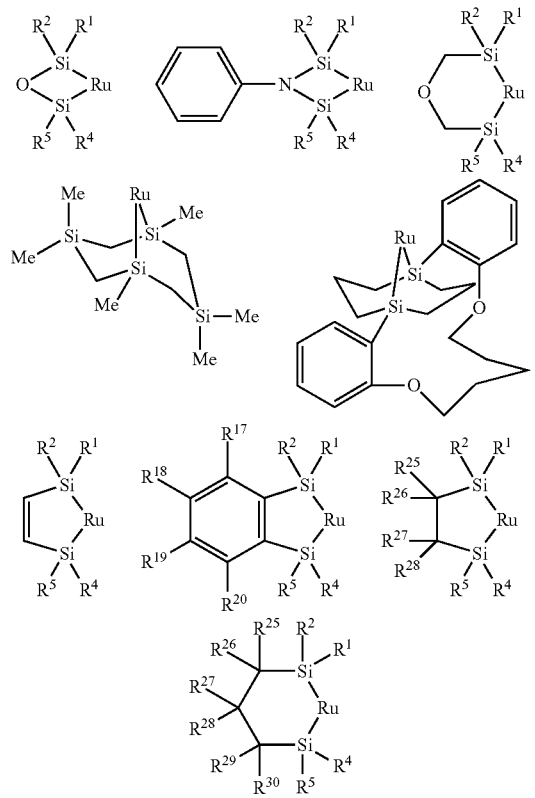

Here, "Me" stands for a methyl group.

In these formulas, $R^1$, $R^2$, $R^4$ and $R^5$ are as defined above, $R^{17}$ to $R^{20}$ (substituent Y) are each independently a hydrogen atom, a halogen atom, an alkyl group of 1 to 10 carbon atoms or an alkoxy group of 1 to 10 carbons, and $R^{25}$ to $R^{30}$ each independently a hydrogen atom or a substituted or unsubstituted monovalent hydrocarbon group of 1 to 20 carbon atoms. $R^{17}$ to $R^{20}$ and $R^{25}$ to $R^{30}$ are preferably hydrogen atoms.

Exemplary of monovalent hydrocarbon groups include alkyl, aryl and aralkyl groups, specific examples of which include the same as those mentioned above.

Specific examples of alkyl groups, alkoxy groups and halogen atoms include the same as those mentioned above.

L represents a two-electron ligand other than CO and thiourea ligands, wherein the two electrons included in the ligand coordinate to ruthenium.

The two-electron ligand is not particularly limited, so long as it is one other than a CO or thiourea ligand; use can be made of any other known ligand that has hitherto been used as a two-electron ligand in metal complexes. Typical examples include compounds such as amines, imines, nitrogen-containing heterocycles, phosphines, phosphites, arsines, alcohols, thiols, ethers and sulfides which contain the unshared electron pair (unpaired electrons) of nitrogen, oxygen, sulfur, phosphorus or the like; π electron-containing alkenes and alkynes; compounds such as aldehydes, ketones, nitriles and isonitriles which contain both unpaired electrons and π electrons; and molecular hydrogen (σ electrons in the H—H bond take part in coordination) and hydrosilane (σ electrons in the Si—H bond take part in coordination) which bond by way of agostic interactions.

In this invention, the coordination number m of the two-electron ligand L is 3 or 4, and is preferably 4.

Examples of amines include tertiary amines of the formula $R_3N$ (wherein each R is independently as defined above).

Examples of imines include those of the formula RC(=NR)R (wherein each R is independently as defined above).

Examples of nitrogen-containing heterocycles include pyrroles, imidazoles, pyridines, pyrimidines, oxazolines and isooxazolines.

Examples of phosphines include those of the formula $R_3P$ (wherein each R is independently as defined above).

Examples of phosphites include those of the formula $(RO)_3P$ (wherein each R is independently as defined above).

Examples of arsines include those of the formula $R_3As$ (wherein each R is independently as defined above).

Examples of alcohols include those of the formula ROH (wherein R is as defined above).

Examples of thiols include those in which the oxygen atom in the above alcohols has been substituted with a sulfur atom.

Examples of ethers include those of the formula ROR (wherein each R is independently as defined above).

Examples of sulfides include those in which the oxygen atom in the above ethers has been substituted with a sulfur atom.

Examples of ethers include those of the formula ROR (wherein each R is independently as defined above).

Examples of sulfides include those in which the oxygen atom in the above ethers has been substituted with a sulfur atom.

Examples of ketones include those of the formula RCOR (wherein each R is independently as defined above).

Examples of isonitriles include those of the formula RNC (wherein each R is as defined above).

Examples of alkenes include those of 2 to 30 carbon atoms, such as ethene, propene, 1-butene, 2-butene, 1-pentene, 2-pentene, cyclopentene, 1-hexene, cyclohexene, 1-heptene, 1-octene, 1-nonene and 1-decene.

Examples of alkynes include those of 2 to 30 carbon atoms, such as ethyne, propyne, 1-butyne, 2-butyne, 1-pentyne, 2-pentyne, 1-hexyne, 1-heptyne, 1-octyne, 1-nonyne and 1-decyne.

Examples of hydrosilanes include triorganohydrosilanes such as tri($C_{1-30}$)organohydrosilanes, and more specifically those of the formula $R^1R^2R^3SiH$ (wherein $R^1$ to $R^3$ are as defined above).

Of these, the two-electron ligands L are preferably molecular hydrogen, amines, imines, nitrogen-containing heterocycles, phosphines, phosphites, alsines, alcohols, thiols, ethers, sulfides, nitriles, isonitriles, aldehydes, ketones, alkenes of 2 to 30 carbon atoms, alkynes of 2 to 30 carbon atoms, or triorganohydrosilanes.

The two L's may bond together to form a ligand containing two coordinating two-electron functional groups. Typical examples include, but are not limited to, ethylenediamine, ethylene glycol dimethyl ether, 1,3-butadiene, and those of the formulas shown below.

However, in the mononuclear ruthenium complex of the invention, when three or more L's are present, they do not assume a structure wherein three L's have bonded together to form a ligand containing three coordinating two-electron functional groups, such as an $\eta^6$-arylene structure.

[Chemical Formula 6]

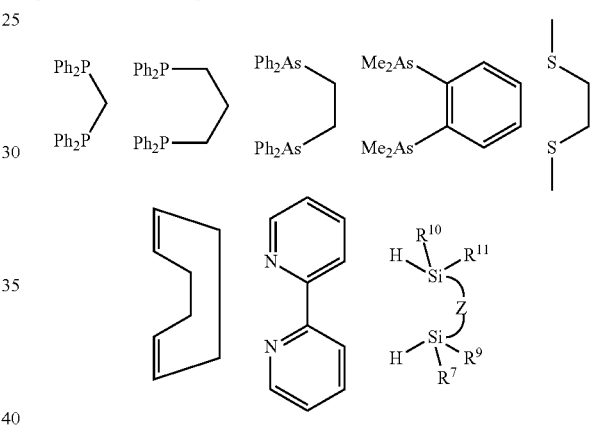

In these formulas, "Me" stands for a methyl group, and "Ph" stands for a phenyl group. $R^7$, $R^9$, $R^{10}$, $R^{11}$ and Z are as defined above.

Moreover, in the mononuclear ruthenium complex of the invention, for reasons having to do with the catalytic activity, at least one two-electron ligand L is preferably of at least one type selected from among isonitriles, amines, imines, nitrogen-containing heterocycles, phosphines, phosphites and sulfides. Letting this two-electron ligand be $L^1$, a mononuclear ruthenium complex of formula (2) is preferred.

[Chemical Formula 7]

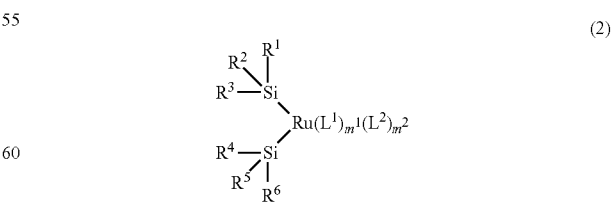

(2)

In formula (2), $R^1$ to $R^6$ are as defined above.

Here, as noted above, $L^1$ is at least one type of two-electron ligand selected from among isonitriles, amines, imines, nitrogen-containing heterocycles, phosphines, phosphites and sulfides. Of these, $L^1$ is more preferably of at least one type selected from among isonitriles, nitrogen-containing heterocycles, phosphines and phosphites; even more preferably of at least one type selected from among isonitriles, nitrogen-containing heterocycles and phosphites; and most preferably an isonitrile having the same electron configuration as carbon monoxide.

The subscript $m^1$ is an integer from 1 to 4, and is preferably 2. When $m^1$ is from 2 to 4, two $L^1$ ligands may be bonded to one another.

Examples of isonitriles include, as mentioned above, those of the formula RNC (wherein each R is as defined above). In particular, R is preferably a substituted or unsubstituted alkyl group of 1 to 10 carbon atoms, aryl group of 6 to 20 carbon atoms or aralkyl group of 7 to 20 carbon atoms; more preferably an aryl group of 6 to 10 carbon atoms; and even more preferably a phenyl group having a substituent such as an alkyl group of 1 to 10 carbons.

Isonitriles that may be used include, but are not limited to, alkyl isocyanides such as methyl isocyanide, ethyl isocyanide, n-propyl isocyanide, cyclopropyl isocyanide, n-butyl isocyanide, isobutyl isocyanide, sec-butyl isocyanide, t-butyl isocyanide, n-pentyl isocyanide, isopentyl isocyanide, neopentyl isocyanide, n-hexyl isocyanide, cyclohexyl isocyanide, cycloheptyl isocyanide, 1,1-dimethylhexyl isocyanide, 1-adamantyl isocyanide and 2-adamantyl isocyanide; aryl isocyanides such as phenyl isocyanide, 2-methylphenyl isocyanide, 4-methylphenyl isocyanide, 2,4-dimethylphenyl isocyanide, 2,5-dimethylphenyl isocyanide, 2,6-dimethylphenyl isocyanide, 2,4,6-trimethylphenyl isocyanide, 2,4,6-tri-t-butylphenyl isocyanide, 2,6-diisopropylphenyl isocyanide, 1-naphthyl isocyanide, 2-naphthyl isocyanide and 2-methyl-1-naphthyl isocyanide; and aralkyl isocyanides such as benzyl isocyanide and phenylethyl isocyanide.

The nitrogen-containing heterocycles are exemplified in the same way as above. Of these, a pyridine ring is preferred.

Pyridine ring-containing compounds that may be used include, but are not limited to, pyridines such as pyridine, 2-methylpyridine, 3-methylpyridine, 4-methylpyridine and 2,6-dimethylpyridine; and bipyridines such as 2,2'-bipyridine, 4,4'-dimethyl-2,2'-bipyridine, 5,5'-dimethyl-2,2'-bipyridine, 4,4'-diethyl-2,2'-bipyridine and 4,4'-di-tert-butyl-2,2'-bipyridine.

Phosphites, as noted above, are exemplified by compounds of the formula (RO)$_3$P (wherein each R is independently as defined above). In particular, phosphites in which R is a substituted or unsubstituted alkyl group of 1 to 10 carbon atoms or an aryl group of 6 to 20 carbon atoms are preferred; those in which R is an alkyl group of 1 to 10 carbon atoms are even more preferred.

Phosphite compounds that may be used include, but are not limited to, trialkylphosphites such as trimethylphosphite, triethylphosphite, triisopropylphosphite, tri-n-butylphosphite, tris(2-ethylhexyl)phosphite, tri-n-decylphosphite, 4-methyl-2,6,7-trioxa-1-phosphabicyclo[2.2.2]octane (trimethylolethane cyclic phosphite) and 4-ethyl-2,6,7-trioxa-1-phosphabicyclo[2.2.2]octane (trimethylolpropane phosphite), alkylarylphosphites such as methyldiphenylphosphite, and triarylphosphites such as triphenylphosphite.

$L^2$ represents a two-electron ligand other than CO and thiourea ligands and other than $L^1$, and is exemplified in the same way as L above. The subscript $m^2$ is an integer from 0 to 3, and is preferably 2. Also, as with m above, the sum $m^1+m^2$ is 3 or 4, and preferably 4. When $m^2$ is 2 or 3, two $L^2$ ligands may be bonded to one another.

In this invention, given that, for reasons having to do with the catalytic activity, it is advantageous for the two-electron ligand $L^2$ to be a ligand that bonds relatively weakly to ruthenium, of the exemplary L ligands mentioned above, thiols, sulfides and triorganohydrosilanes in particular are more preferred. Two triorganohydrosilanes of the formulas SiHR$^7$R$^8$R$^9$ and SiHR$^{10}$R$^{11}$R$^{12}$ (wherein R$^7$ to R$^{12}$ are each independently an alkyl, aryl or aralkyl group that may be substituted with X, which is as defined above), and two sulfides or thiols of the formulas SR$^{13}$R$^{14}$ and SR$^{15}$R$^{16}$ (wherein R$^{13}$ to R$^{16}$ are each independently a hydrogen atom or an alkyl, aryl or aralkyl group that may be substituted with X, which is as defined above) are even more preferred.

Here, the alkyl, aryl and aralkyl groups are exemplified by the same groups as mentioned earlier, with alkyl groups of 1 to 10 carbon atoms, aryl groups of 6 to 20 carbon atoms and aralkyl groups of 7 to 20 carbon atoms being respectively preferred, and alkyl groups of 1 to 10 carbon atoms and aryl groups of 6 to 20 carbon atoms being more preferred.

When the mononuclear ruthenium complex of formula (2) has, for example, two $L^1$ ligands and two $L^2$ ligands (these being distinguished as $L^{2a}$ and $L^{2b}$), geometric isomers such as those shown in the formulas below are present. The mononuclear ruthenium complex of the invention encompasses all of these geometric isomers.

[Chemical Formula 8]

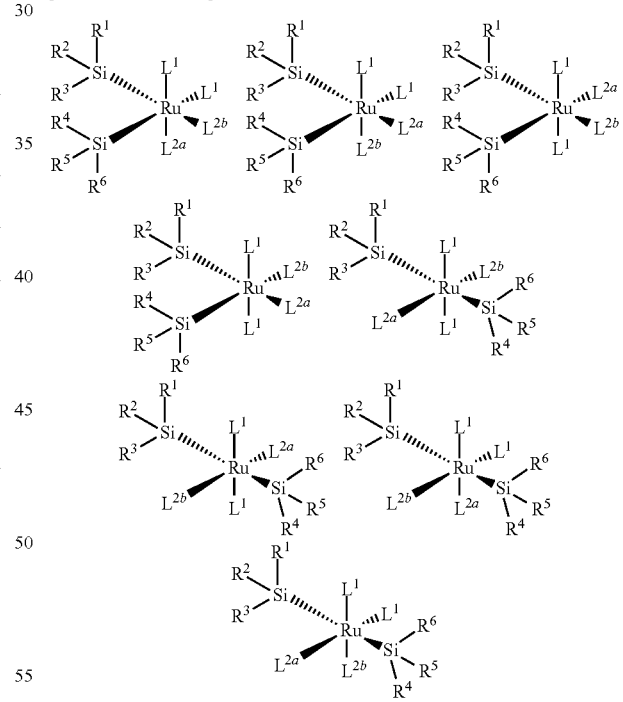

Here, R$^1$ to R$^6$ and L$^1$ are as defined above, and $L^{2a}$ and $L^{2b}$ are as defined above for $L^2$.

When the $L^2$ ligands are triorganohydrosilanes of the formulas SiHR$^7$R$^8$R$^9$ and SiHR$^{10}$R$^{11}$R$^{12}$ (R$^7$ to R$^{12}$ being as defined above), two or more of the four silicon atoms in the mononuclear ruthenium complex may be connected together by the above-described crosslinking substituents Z. The silicon atom combinations may be any of the following: a combination of silicon atoms having silicon-ruthenium covalent bonds, a combination of silicon atoms in Si—H bond coordination, or a combination of a silicon atom having a silicon-ruthenium covalent bond with a silicon atom in Si—H bond coordination. The number of Z substituents that connect together two silicon atoms is from 1 to 3, and the total number of Z substituents included in the overall complex is from 1 to 12.

When a mononuclear ruthenium complex having such crosslinked substituents Z is expressed using a single coordination geometry, examples include, but are not limited to, the geometries indicated by the following formulas. As mentioned above, geometric isomers other than these also exist; geometries having similar crosslinked substituents Z exist in such cases as well.

[Chemical Formula 9]

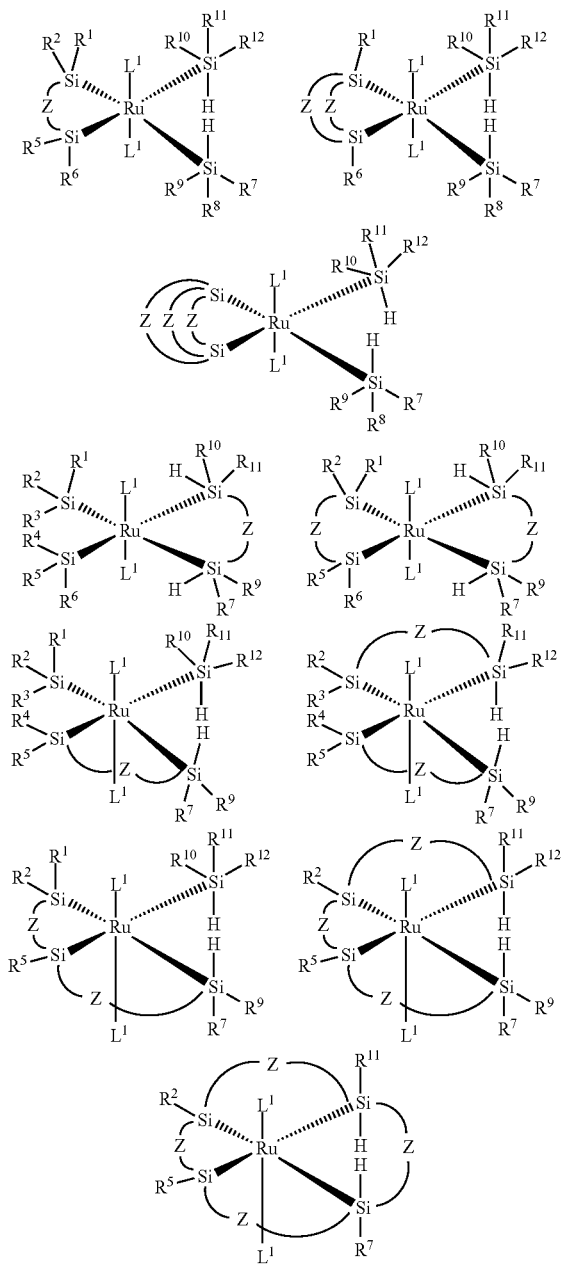

In these formulas, $R^1$ to $R^{12}$, $L^1$ and Z are as defined above.

Mononuclear ruthenium complex geometries having a specific disilametallocycle structure are exemplified by, but not limited to, those of the following formulas (shown with $L^1$ omitted).

[Chemical Formula 10]

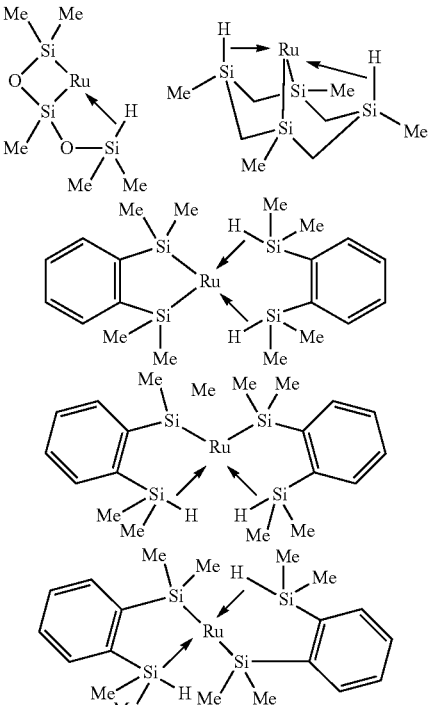

Here, "Me" stands for a methyl group.

In this invention, mononuclear ruthenium complexes with two $L^1$ ligands coordinated to the ruthenium and also agostic Si—H coordination of triorganohydrosilanes (two-electron ligands) are especially preferred. Using, for the sake of convenience, a single coordination geometry to represent such ruthenium complexes, exemplary geometries include those of formula (3). However, as noted above, geometric isomers other than this are acceptable as well in the invention.

[Chemical Formula 11]

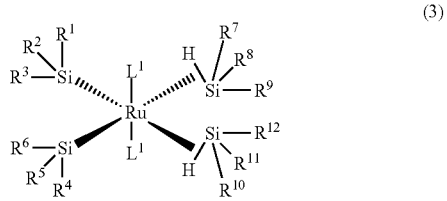

(3)

In the formula, $L^1$ is as defined above.

In formula (3), $R^1$ to $R^{12}$ are as defined above, although it is preferable for $R^1$ to $R^6$ to each be independently an alkyl, aryl or aralkyl group that may be substituted with X, which is as defined above.

Here, the alkyl, aryl and aralkyl groups are exemplified by the same groups as mentioned above, with alkyl groups of 1 to 10 carbon atoms, aryl groups of 6 to 20 carbon atoms and aralkyl groups of 7 to 20 carbon atoms being preferred, and alkyl groups of 1 to 10 carbon atoms and aryl groups of 6 to 20 carbon atoms being more preferred.

In above formula (3), two or more of the four silicon atoms in the mononuclear ruthenium complex may be connected together by crosslinking substituents. Specifically, at least one pair of any of $R^1$ to $R^3$ and any of $R^4$ to $R^6$ or any of $R^7$ to $R^9$, or at least one pair of any of $R^{10}$ to $R^{12}$ and any of $R^4$ to $R^6$ or any of $R^7$ to $R^9$, may bond together to form a crosslinking substituent that is an alkylene, arylene or aralkylene group. Alternatively, at least one pair of any of $R^1$ to $R^3$ and any of $R^4$ to $R^6$ or any of $R^7$ to $R^9$ may bond together to form a crosslinking substituent that is an alkylene, arylene or aralkylene group, and also at least one pair of any of $R^{10}$ to $R^{12}$ with any of $R^4$ to $R^6$ or any of $R^7$ to $R^9$ may bond together to form a crosslinking substituent that is an alkylene, arylene or aralkylene group.

Here, the alkylene, arylene and aralkylene groups are exemplified by the same groups as mentioned earlier, With alkylene groups of 1 to 10 carbon atoms, arylene groups of 7 to 20 carbon atoms and aralkylene groups of 7 to 20 carbon atoms being preferred, and alkylene groups of 1 to 6 carbon atoms and arylene groups of 7 to 20 carbon atoms being more preferred.

Mononuclear ruthenium complexes that may be suitably used in the invention, as represented using typical coordination geometries, are exemplified by those of formulas (4) and (5). Illustrative examples include, but are not limited to, those of formulas (6) to (11), and more specifically those of formulas A to F. In addition, as mentioned above, geometric isomers of these may also be suitably used.

[Chemical Formula 12]

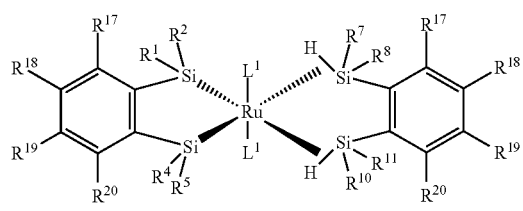
(4)

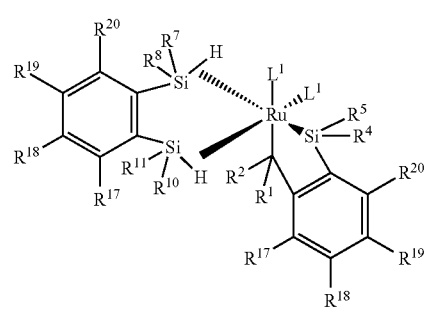
(5)

In formulas (4) and (5), $R^1$, $R^2$, $R^4$, $R^5$, $R^7$, $R^8$, $R^{10}$, $R^{11}$, $R^{17}$ to $R^{20}$, and $L^1$ are as defined above.

[Chemical Formula 13]

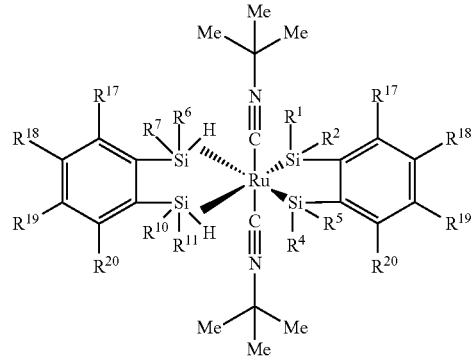
(6)

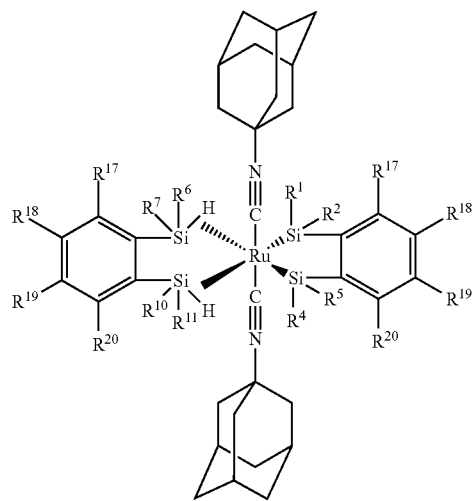
(7)

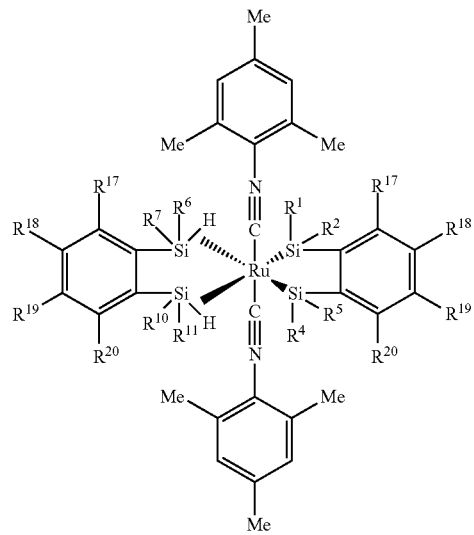
(8)

-continued
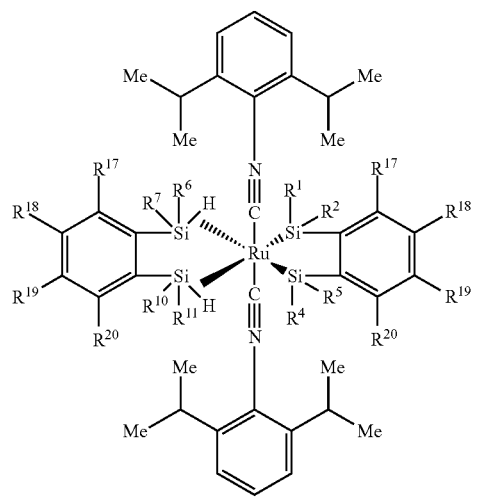
(9)
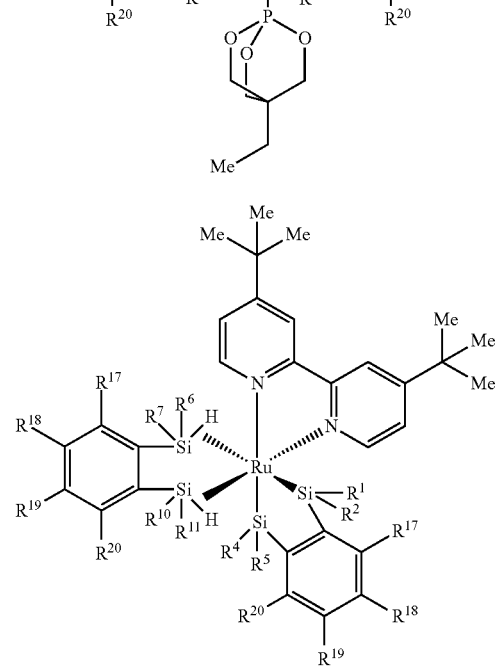
(10)
(11)
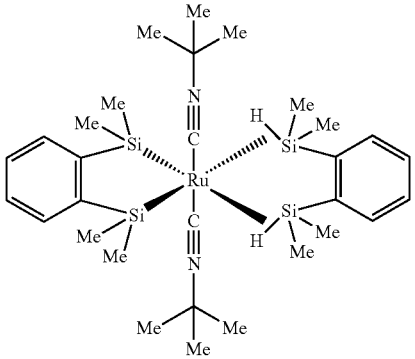
A
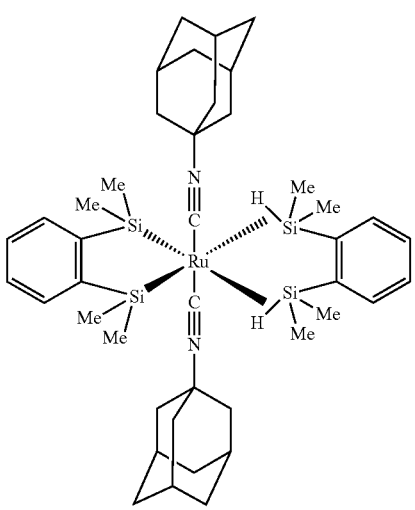
B
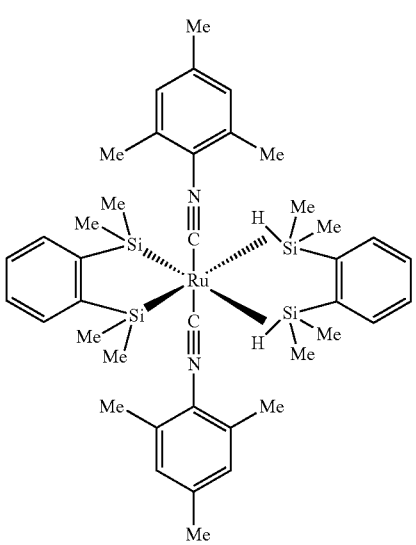
C
[Chemical Formula 14]
In formulas (6) to (11), $R^1$, $R^2$, $R^4$, $R^5$, $R^6$, $R^7$, $R^{10}$, $R^{11}$, and $R^{17}$ to $R^{20}$ are as defined above. "Me" stands for a methyl group.

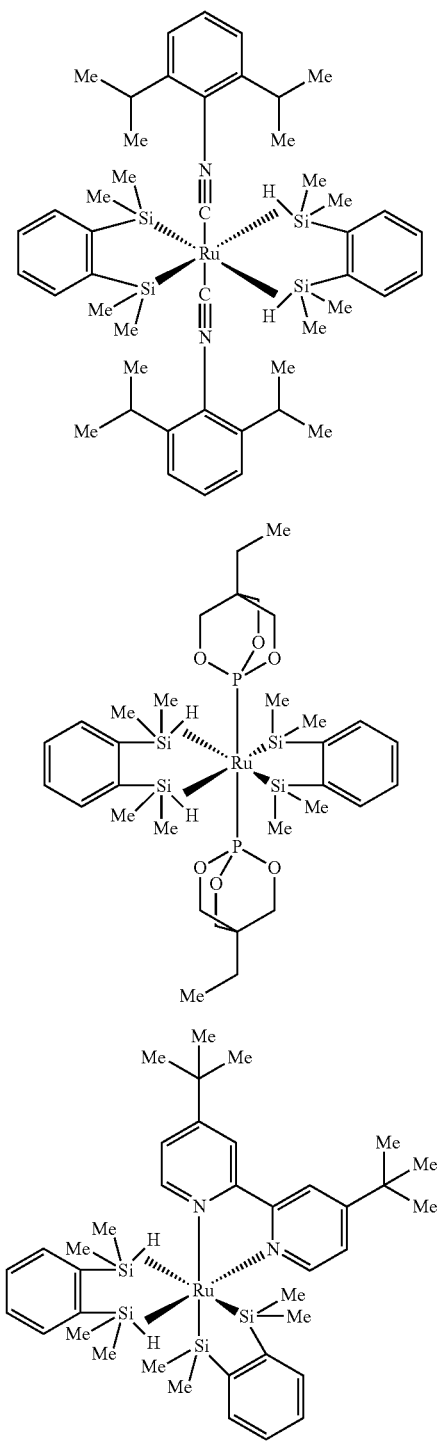

Here, "Me" stands for a methyl group.

The mononuclear ruthenium complex of the invention can be prepared by a combination of known organic synthesis reactions.

For example, above ruthenium complexes A to F can be obtained by reacting, in an inert gas atmosphere such as argon gas and within an organic solvent: a ruthenium-olefin complex which contains as ligands a cycloalkadienyl group such as cyclohexadienyl or cyclooctadienyl and an alkenyl group such as allyl or 2-methylallyl, with a bis(silyl) compound such as 1,2-bis(dimethylsilyl)benzene and an isonitrile compound such as t-butyl isocyanide, a phosphite compound or a bipyridine compound.

The amount of bis(silyl) compound used may be set to from about 1 to 10 moles, and preferably 2 to 5 moles, per mole of the ruthenium-olefin complex.

The amount of isonitrile compound, phosphite compound or bipyridine compound used may be set to from about 1 to 10 moles, and preferably 2 to 5 moles, per mole of the ruthenium-olefin complex.

Various types of solvents may be used as the organic solvent, provided they do not adversely affect the reaction. Illustrative examples include aliphatic hydrocarbons such as pentane, hexane, heptane, octane and cyclohexane; ethers such as diethyl ether, diisopropyl ether, dibutyl ether, cyclopentyl methyl ether, tetrahydrofuran and 1,4-dioxane; and aromatic hydrocarbons such as benzene, toluene, xylene and mesitylene.

The reaction temperature should be suitably set in the range of the melting point to the boiling point of the organic solvent, and is preferably from 10 to 100° C., and more preferably from 30 to 80° C.

The reaction time is generally from about 1 to about 48 hours.

Following reaction completion, the solvent is distilled off, after which the target substance can be obtained by a known purification method such as re-crystallization, although use as the intended reaction catalyst without isolating the prepared ruthenium complex is possible.

The mononuclear ruthenium complexes of the invention, as already mentioned, exhibit a catalytic activity in at least any one of the following types of reactions: hydrosilylation reactions, hydrogenation reactions and carbonyl compound reduction reactions, although some mononuclear ruthenium complexes of the invention exhibit catalytic activities in two of these types of reactions, and some even exhibit catalytic activities in all three types of reactions.

In cases where, using a mononuclear ruthenium complex of the invention as the catalyst, a hydrosilylation reaction is carried out between an aliphatic unsaturated bond-containing compound such as an aliphatic unsaturated bond-containing olefin compound, silane compound or organopolysiloxane compound and an Si—H bond-containing silane compound or organopolysiloxane compound, the amount of catalyst used is not particularly limited. However, to induce the reaction to proceed under mild conditions of room temperature to about 100° C. and obtain the target substance in a good yield, it is preferable for the amount of catalyst used to be set to at least 0.005 mol %.

In those cases as well where, using a mononuclear ruthenium complex of the invention as the catalyst, a reaction is carried out that reduces an aliphatic unsaturated bond-containing olefin compound with hydrogen gas to obtain a saturated compound, the amount of catalyst used is not particularly limited. However, to induce the reaction to proceed under mild conditions of room temperature and a hydrogen pressure of about 1 atmosphere and obtain the target substance in a good yield, it is preferable for the amount of catalyst used to be set to at least 0.05 mol %.

In those cases as well where, using a mononuclear ruthenium complex of the invention as the catalyst, a carbonyl compound is reduced with an Si—H group-containing silane or siloxane, the amount of catalyst used is not particularly limited. However, to induce the reaction to proceed under mild conditions and obtain the target substance in a good yield, it is preferable for the amount of catalyst used to be set to at least 0.1 mol %.

Examples of carbonyl compounds that may be furnished to the reducing reaction include compounds having amide, aldehyde, ketone, ester, carboxylic acid or carboxylic acid salt (e.g., sodium salt, potassium salt) groups. By reacting these with a Si—H group-containing silane or siloxane in the presence of a ruthenium complex catalyst of the invention, derivation to the respective corresponding amine or alcohol compounds is possible.

In all of these reactions, the amount of catalyst used is not subject to any upper limit, although for economic reasons, the maximum amount is about 5 mol %.

EXAMPLES

Working Examples are given below to more concretely illustrate the invention, although the invention is not limited by these Examples.

All of the operations in synthesis of the ruthenium complexes were carried out in an argon atmosphere using the Schlenk technique or a glove box. The solvents used in preparation of the transition metal compounds were all used following deoxygenation and dehydration by known methods.

Alkene hydrosilylation reactions, hydrogenation reactions, amide reduction reactions and solvent purification were all carried out in an inert gas atmosphere. The solvents used in these various reactions were all purified, dried and deoxygenated beforehand by known methods.

$^1$H, $^{13}$C and $^{29}$Si-NMR measurements were carried out with JNM-ECA600 and JNM-LA400 systems from JEOL Ltd., IR measurements were carried out with an FT/IR-550 system from JASCO Corporation, elemental analyses were carried out with a Perkin-Elmer 2400 II/CHN analyzer, and x-ray crystallographic analyses were carried out with a VariMax system from Rigaku Corporation using MoKα radiation (=0.71069 Å).

In the chemical structural formulas shown below, hydrogen atoms are omitted in accordance with standard nomenclature. "Me" stands for methyl.

(1) Synthesis of Ruthenium Complexes

[Working Example 1] Synthesis of Ruthenium Complex a

[Chemical Formula 15]

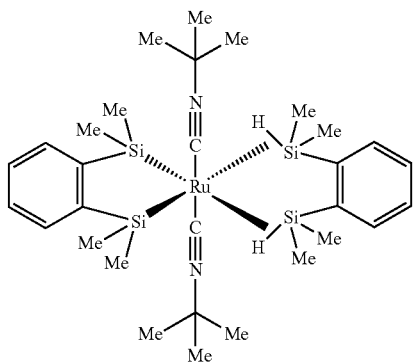

Under an argon atmosphere, a 100 mL Schlenk tube was charged with (η$^4$-1,5-cyclooctadiene)ruthenium(II) bis(η$^3$-2-methylallyl) complex (200 mg, 0.63 mmol), 1,2-bis(dimethylsilyl)benzene (243 mg, 1.26 mmol) and t-butyl isocyanide (104 mg, 1.26 mmol). Degassed and dehydrated hexane (30 mL) was added thereto and the system was stirred at 55° C. for 18 hours. Following reaction completion, the system was dried in vacuo and the resulting dried product was dissolved in hexane (40 mL); the small amount of brown insoluble matter that formed as by-product was removed by centrifugal separation. Next, the hexane solution was dried in vacuo and washed with hexamethyldisiloxane (10 mL), and the remaining white powder was dissolved in 10 mL of hexane and re-crystallized at −35° C., giving Ruthenium Complex A (49 mg/0.08 mmol/12%) which is typically represented by the above formula. FIG. 1 shows the structure of the Ruthenium Complex A obtained, and FIG. 2 shows the results of $^1$H-NMR measurement.

$^1$H-NMR (C$_6$D$_6$, 600 MHz) δ=−7.64 (br s, 2H, Si—H), 0.59 (s, 18H, CMe$_3$), 0.94 (s, 24H, SiMe$_2$), 7.33-7.38 (m, 4H, C$_6$H$_4$), 7.81-7.86 (m, 4H, C$_6$H$_4$).

$^{29}$Si-NMR (C$_6$D$_6$, 119 MHz) 5=27.2.

IR (KBr pellet): ν=1930 (ν$_{Si-H}$), 2116 (ν$_{Ru-CN}$)cm$^{-1}$.

Analysis:

Calculated for C$_{30}$H$_{52}$N$_2$RuSi$_4$: C, 55.08; H, 8.01; N, 4.28.

Found: C, 55.21; H, 7.89; N, 4.01.

[Working Example 2] Synthesis of Ruthenium Complex B

[Chemical Formula 16]

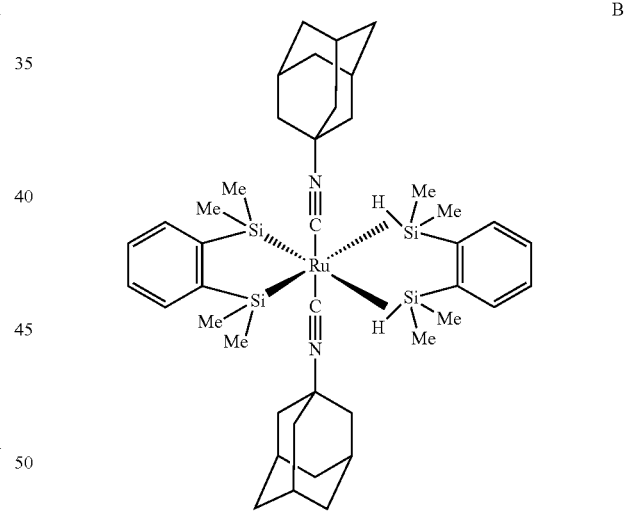

Under an argon atmosphere, a 100 mL Schlenk tube was charged with (η$^4$-1,5-cyclooctadiene)ruthenium(II) bis(η$^3$-2-methylallyl) complex (200 mg, 0.63 mmol), 1,2-bis(dimethylsilyl)benzene (243 mg, 1.26 mmol) and 1-isocyanoadamantane (203 mg, 1.26 mmol). Degassed and dehydrated hexane (30 mL) was added thereto and the system was stirred at 55° C. for 18 hours. Following reaction completion, the system was dried in vacuo and the resulting dried product was dissolved in hexane (40 mL); the small amount of brown insoluble matter that formed as by-product was removed by centrifugal separation. Next, the hexane solution was dried in vacuo, washed with hexamethyldisiloxane (10 mL), and the remaining white powder was dissolved in 10 mL of hexane and re-crystallized at −35° C., giving Ruthenium Complex B (51 mg/0.06 mmol/10%) which is typically represented by the above formula. FIG. 3 shows the structure of the Ruthenium Complex B obtained, and FIG. 4 shows the results of $^1$H-NMR measurement.

$^1$H-NMR (C$_6$D$_6$, 600 MHz) δ=−7.62 (br s, 2H, Si—H), 0.93-1.09 (m, 12H, CH$_2$), 1.04 (s, 24H, SiMe$_2$), 1.38-1.44 (br s, 18H, CH$_2$ and CH of adamantyl), 7.34-7.41 (m, 4H, C$_6$H$_4$), 7.87-7.92 (m, 4H, C$_6$H$_4$).

$^{29}$Si-NMR (C$_6$D$_6$, 119 MHz)δ=21.1.

IR (KBr pellet): ν=1928 (ν$_{Si-H}$), 2118 (ν$_{Ru-CN}$) cm$^{-1}$.

Analysis:

Calculated for C$_{42}$H$_{64}$N$_2$RuSi$_4$: C, 62.25; H, 7.96; N, 3.46.

Found: C, 62.53; H, 8.24; N, 3.22.

[Working Example 3] Synthesis of Ruthenium Complex C

[Chemical Formula 17]

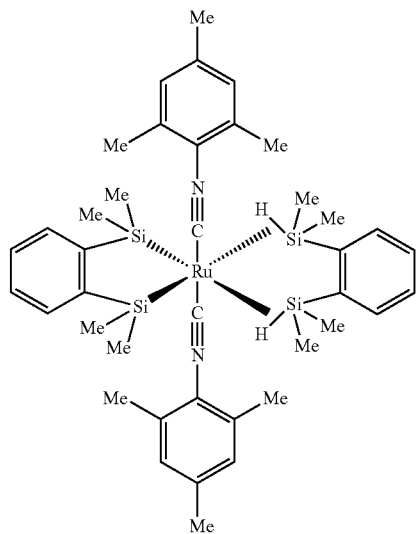

C

Under an argon atmosphere, a 100 mL Schlenk tube was charged with (η$^4$-1,5-cyclooctadiene)ruthenium(II) bis(η$^3$-2-methylallyl) complex (200 mg, 0.63 mmol), 1,2-bis(dimethylsilyl)benzene (243 mg, 1.26 mmol) and 2,4,6-trimethylphenyl isocyanide (183 mg, 1.26 mmol). Degassed and dehydrated hexane (30 mL) was added thereto and the system was stirred at 55° C. for 18 hours. Following reaction completion, the system was dried in vacuo and the resulting dried product was dissolved in toluene (40 mL); the small amount of brown insoluble matter that formed as by-product was removed by centrifugal separation. Next, the toluene solution was dried in vacuo, washed with hexane (10 mL), and the remaining white powder was dissolved in 5 mL of toluene and re-crystallized at −35° C., giving Ruthenium Complex C (74 mg/0.09 mmol/10%) which is typically represented by the above formula. FIG. 5 shows the results of the $^1$H-NMR measurement of the resulting Ruthenium Complex C.

$^1$H-NMR (C$_6$D$_6$, 600 MHz) δ=−7.05 (br s, 2H, Si—H), 1.02 (s, 24H, SiMe$_2$), 1.75 (s, 6H, para-Me of C$_6$H$_2$Me$_3$), 1.76 (s, 12H, ortho-Me of C$_6$H$_2$Me$_3$), 6.20 (s, 4H, C$_6$H$_2$Me$_3$), 7.36-7.39 (m, 4H, C$_6$H$_4$), 7.81-7.85 (m, 4H, C$_6$H$_4$).

IR (KBr pellet): ν=1917 (ν$_{Si-H}$), 2082 (ν$_{Ru-CN}$) cm$^{-1}$.

Analysis:

Calculated for C$_{40}$H$_5$N$_2$RuSi$_4$: C, 61.73; H, 7.25; N, 3.60.

Found: C, 61.86; H, 7.02; N, 3.82.

[Working Example 4] Synthesis of Ruthenium Complex D

[Chemical Formula 18]

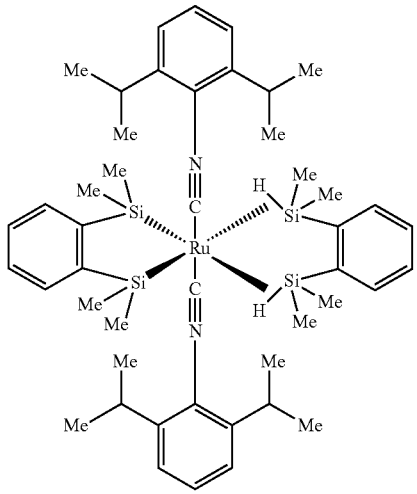

D

Under an argon atmosphere, a 100 mL Schlenk tube was charged with (η$^4$-1,5-cyclooctadiene)ruthenium(II) bis(η$^3$-2-methylallyl) complex (200 mg, 0.63 mmol), 1,2-bis(dimethylsilyl)benzene (243 mg, 1.26 mmol) and 2,6-diisopropylphenyl isocyanide (236 mg, 1.26 mmol). Degassed and dehydrated hexane (30 mL) was added thereto and the system was stirred at 55° C. for 18 hours. Following reaction completion, the system was dried in vacuo and the resulting dried product was dissolved in tetrahydrofuran (40 mL, referred to below as "THF"); the small amount of brown insoluble matter that formed as by-product was removed by centrifugal separation. Next, the THF solution was dried in vacuo, washed with hexane (10 mL), and the remaining white powder was dissolved in 5 mL of THF and re-crystallized at −35° C., giving Ruthenium Complex D (60 mg/0.07 mmol/11%) which is typically represented by the above formula. FIG. 6 shows the results of the $^1$H-NMR measurement of the resulting Ruthenium Complex D.

$^1$H-NMR (C$_6$D$_6$, 600 MHz) δ=−7.09 (br s, 2H, Si—H), 0.78 (d, J$_{H-H}$=6.9 Hz, 24H, CHMe$_2$), 0.99 (s, 24H, SiMe$_2$), 2.92 (sept, J$_{H-H}$=6.9 Hz, 4H, CHMe$_2$), 6.70 (d, J$_{H-H}$=6.9 Hz, 4H, meta-C$_6$H$_3$), 6.82 (t, J$_{H-H}$=6.9 Hz, 2H, para-C$_6$H$_3$), 7.32-7.36 (m, 4H, C$_6$H$_4$), 7.78-7.83 (m, 4H, C$_6$H$_4$).

IR (KBr pellet): ν=1928 (ν$_{Si-H}$), 2081 (ν$_{Ru-CN}$) cm$^{-1}$.

Analysis:

Calculated for C$_{46}$H$_8$N$_2$RuSi$_4$: C, 64.06; H, 7.95; N, 3.25.

Found: C, 63.87; H, 8.34; N, 3.62.

[Working Example 5] Synthesis of Ruthenium Complex E

[Chemical Formula 19]

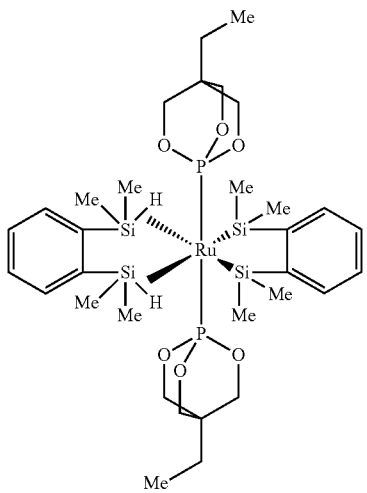

Under an argon atmosphere, a 100 mL Schlenk tube was charged with (η$^4$-1,5-cyclooctadiene)ruthenium (II) bis(η$^3$-2-methylallyl) complex (200 mg, 0.63 mmol), 1,2-bis(dimethylsilyl)benzene (243 mg, 1.26 mmol) and trimethylolpropane phosphite (204 mg, 1.26 mmol). Degassed and dehydrated hexane (30 mL) was added thereto and the system was stirred at 55° C. for 18 hours. Following reaction completion, the system was dried in vacuo and the resulting dried product was dissolved in toluene (40 mL); the small amount of brown insoluble matter that formed as by-product was removed by centrifugal separation. Next, the toluene solution was dried in vacuo, washed with hexane (10 mL), and the remaining white powder was dissolved in 10 mL of toluene and re-crystallized at −35° C., giving Ruthenium Complex E (61 mg/0.08 mmol/12%) which is typically represented by the above formula. FIG. 7 shows the structure of the Ruthenium Complex E obtained, and FIG. 8 shows the results of $^1$H-NMR measurement.

$^1$H-NMR (C$_6$D$_6$, 600 MHz) δ=−8.52 (t, J$_{H-P}$=12.6 Hz, 2H, Si—H), −0.16 (t, =6.9 Hz, 6H, CH$_2$C$\underline{H}_3$), 0.06 (q, J$_{H-H}$=6.9 Hz, 4H, C$\underline{H}_2$CH$_3$), 1.13 (s, 24H, SiMe$_3$), 3.03 (s, 12H, OCH$_2$), 7.28-7.34 (m, 4H, C$_6$H$_4$), 7.81-7.86 (m, 4H, C$_6$H$_4$).

$^{29}$Si-NMR (C$_6$D$_6$, 119 MHz) δ=27.7.

[Working Example 6] Synthesis of Ruthenium Complex F

[Chemical Formula 20]

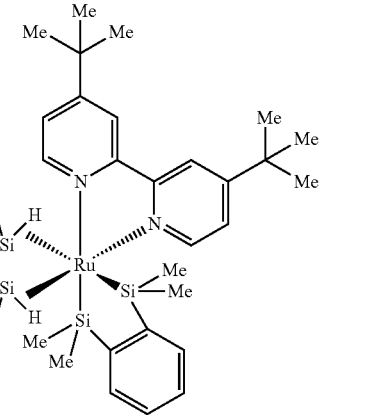

Under an argon atmosphere, a 100 mL Schlenk tube was charged with (η$^4$-1,5-cyclooctadiene)ruthenium(II) bis(η$^3$-2-methylallyl) complex (200 mg, 0.63 mmol), 1,2-bis(dimethylsilyl)benzene (243 mg, 1.26 mmol) and 4,4'-di-t-butyl-2,2'-bipyridine (169 mg, 0.63 mmol). Degassed and dehydrated hexane (30 mL) was added thereto and the system was stirred at 55° C. for 18 hours. Following reaction completion, the system was dried in vacuo and the resulting dried product was dissolved in toluene (50 mL); the small amount of brown insoluble matter that formed as by-product was removed by centrifugal separation. Next, the toluene solution was dried in vacuo, washed with hexane (10 mL), and the remaining red powder was dissolved in 30 mL of toluene and re-crystallized at −35° C., giving Ruthenium Complex F (67 mg/0.09 mmol/14%) which is typically represented by the above formula. FIG. 9 shows the structure of the Ruthenium Complex E obtained, and FIG. 10 shows the results of $^1$H-NMR measurement.

$^1$H-NMR (C$_6$D$_6$, 600 MHz) δ=−11.2 (t, J$_{H-Si}$=12.4 Hz, 2H, Si—H), −0.07-1.05 (br s, 24H, SiMe$_2$), 0.87 (s, 18H, C(CH$_3$)$_3$), 6.45 (d, J$_{H-H}$=6.9 Hz, 2H, C$_5$H$_3$N), 7.21-7.27 (m, 4H, C$_6$H$_4$), 7.58-7.70 (br s, 4H, C$_6$H$_4$), 8.00 (s, 2H, C$_5$H$_3$N), 8.53 (d, J$_{H-H}$=6.9 Hz, 2H, C$_5$H$_3$N).

$^{29}$Si-NMR (C$_6$D$_6$, 119 MHz) δ=13.2.

IR (KBr pellet): ν=2028 (ν$_{si-H}$) cm$^{-1}$.

Analysis:

Calculated for C$_{38}$H$_{58}$N$_2$RuSi$_4$: C, 60.35; H, 7.73; N, 3.70.

Found: C, 60.03; H, 7.56; N, 3.46.

(2) Hydrosilylation of Styrene with 1,1,1,3,3-Pentamethyldiloxane Using Ruthenium Complexes

[Chemical Formula 21]

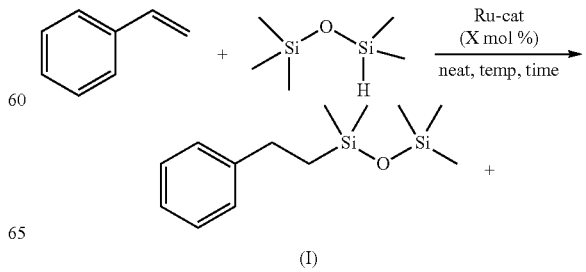

(I)

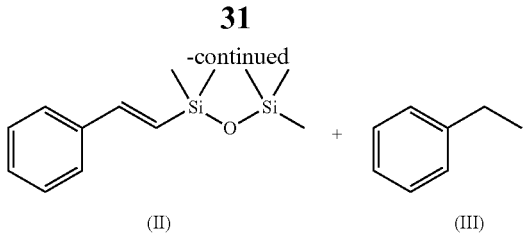

(II)    (III)

[Working Example 7] Hydrosilylation Reaction Using Ruthenium Complex A

A magnetic stirrer was placed in a 20 mL Schlenk tube and the tube was dried by heating under a reduced pressure of 5 Pa, after which the tube interior was purged with argon. Ruthenium Complex A (6.5 mg, 0.01 mmol) was added as the catalyst to this Schlenk tube. Styrene (104 mg, 1.0 mmol) was added thereto, followed by 1,1,1,3,3-pentamethyldisiloxane (163 mg, 1.1 mmol), and the resulting solution was stirred at 25° C. for 23 hours. After cooling of the solution, anisole (108 mg, 1.0 mmol) was added as an internal reference, the $^1$H-NMR spectrum was measured, and the structure and yield of the product were determined. These results are shown as Entry 1 in Table 1.

1,1,1,3,3-Pentamethyl-3-(2-phenylethyl)-disiloxane (Compound (I) above):

$^1$H-NMR (400 MHz, CDCl$_3$) δ=−0.03 (s, 6H, Si(CH$_3$)$_2$), −0.02 (s, 9H, Si(CH$_3$)$_2$) 0.775-0.81 (m, 2H, SiCH$_2$), 2.52-2.57 (m, 2H, CH$_2$C$_6$H$_5$), 7.09-7.13 (m, 2H, C$_6$H$_5$), 7.17-7.22 (m, 3H, C$_6$H$_5$).

1,1,1,3,3-Pentamethyl-3-[(1E)-2-phenylethenyl]-disiloxane (Compound (II) above):

$^1$H-NMR (400 MHz, CDCl$_3$) δ=0.11 (s, 6H, Si(CH$_3$)$_2$), 0.22 (s, 9H, Si(CH$_3$)$_3$), 6.42 (d, $J_{H-H}$=19.3 Hz, 1H, —CH=CH—), 6.93 (d, $J_{H-H}$=19.3 Hz, 1H, —CH=CH—), 7.24-7.29 (m, 1H, C$_6$H$_5$), 7.31-7.39 (m, 2H, C$_6$H$_5$), 7.43-7.47 (m, 2H, C$_6$H$_5$).

Ethylbenzene (Compound (III) above):

$^1$H-NMR (400 MHz, CDCl$_3$) δ=1.26 (t, 2H, $J_{H-H}$=7.7 Hz, CH$_3$), 2.67 (q, 2H, $J_{H-H}$=7.7 Hz, CH$_2$), 7.16-7.24 (m, 3H, C$_6$H$_5$), 7.27-7.33 (m, 2H, C$_6$H$_5$).

[Working Example 8] Hydrosilylation Reaction Using Ruthenium Complex B

A magnetic stirrer was placed in a 20 mL Schlenk tube and the tube was dried by heating under a reduced pressure of 5 Pa, after which the tube interior was purged with argon. Ruthenium Complex B (2.4 mg, 0.003 mmol) was added as the catalyst to this Schlenk tube. Styrene (104 mg, 1.0 mmol) was added thereto, followed by 1,1,1,3,3-pentamethyldisiloxane (163 mg, 1.1 mmol), and the resulting solution was stirred at 25° C. for 23 hours. After cooling of the solution, anisole (108 mg, 1.0 mmol) was added as an internal reference, the $^1$H-NMR spectrum was measured, and the structure and yield of the product were determined. These results are shown as Entry 2 in Table 1.

[Working Example 9] Hydrosilylation Reaction Using Ruthenium Complex C

A magnetic stirrer was placed in a 20 mL Schlenk tube and the tube was dried by heating under a reduced pressure of 5 Pa, after which the tube interior was purged with argon. Ruthenium Complex C (2.3 mg, 0.003 mmol) was added as the catalyst to this Schlenk tube. Styrene (104 mg, 1.0 mmol) was added thereto, followed by 1,1,1,3,3-pentamethyldisiloxane (163 mg, 1.1 mmol), and the solution was stirred at 25° C. for 23 hours. After cooling of the solution, anisole (108 mg, 1.0 mmol) was added as an internal reference, the $^1$H-NMR spectrum was measured, and the structure and yield of the product were determined. These results are shown as Entry 3 in Table 1.

[Working Example 10] Hydrosilylation Reaction Using Ruthenium Complex D

A magnetic stirrer was placed in a 20 mL Schlenk tube and the tube was dried by heating under a reduced pressure of 5 Pa, after which the tube interior was purged with argon. Ruthenium Complex D (0.9 mg, 0.001 mmol) was added as the catalyst to this Schlenk tube. Styrene (1,040 mg, 10 mmol) was added thereto, followed by 1,1,1,3,3-pentamethyldisiloxane (1,630 mg, 11 mmol), and the resulting solution was stirred at 25° C. for 23 hours. After cooling of the solution, anisole (1,080 mg, 10 mmol) was added as an internal reference, the $^1$H-NMR spectrum was measured, and the structure and yield of the product were determined. These results are shown as Entry 4 in Table 1.

[Working Example 11] Hydrosilylation Reaction Using Ruthenium Complex F

A magnetic stirrer was placed in a 20 mL Schlenk tube and the tube was dried by heating under a reduced pressure of 5 Pa, after which the tube interior was purged with argon. Ruthenium Complex F (2.3 mg, 0.003 mmol) was added as the catalyst to this Schlenk tube. Styrene (104 mg, 1.0 mmol) was added thereto, followed by 1,1,1,3,3-pentamethyldisiloxane (163 mg, 1.1 mmol), and the resulting solution was stirred at 25° C. for 23 hours. After cooling of the solution, anisole (108 mg, 1.0 mmol) was added as an internal reference, the $^1$H-NMR spectrum was measured, and the structure and yield of the product were determined. These results are shown as Entry 5 in Table 1.

TABLE 1

| Entry | Cat | Cat loading (X) (mol %) | Temp. (° C.) | Time (h) | Yield (I) | (II) | (III) |
|---|---|---|---|---|---|---|---|
| 1 | A | 1 | r.t. | 23 | 45 | 28 | 24 |
| 2 | B | 0.3 | r.t. | 23 | 39 | 28 | 28 |
| 3 | C | 0.3 | r.t. | 23 | 43 | 29 | 28 |
| 4 | D | 0.01 | r.t. | 23 | 92 | 2 | 1 |
| 5 | F | 0.3 | r.t. | 23 | trace | 18 | 17 |

(3) Hydrosilylation with Dimethylphenylsilane Using Ruthenium Complexes

[Chemical Formula 22]

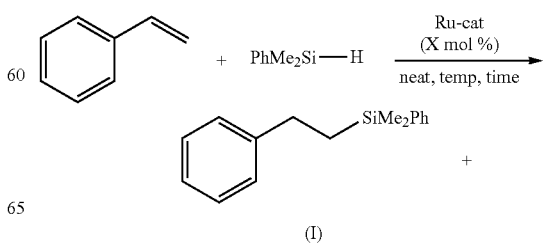

(I)

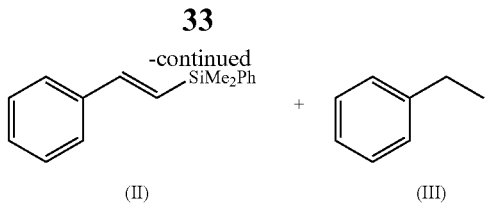

(II)  (III)

[Working Example 12] Hydrosilylation Reaction Using Ruthenium Complex A

A magnetic stirrer was placed in a 20 mL Schlenk tube and the tube was dried by heating under a reduced pressure of 5 Pa, after which the tube interior was purged with argon. Ruthenium Complex A (3.2 mg, 0.005 mmol) was added as the catalyst to this Schlenk tube. Styrene (1,040 mg, 10 mmol) was added thereto, followed by dimethylphenylsilane (1,500 mg, 11 mmol), and the resulting solution was stirred at 25° C. for 23 hours. After cooling of the solution, anisole (1,080 mg, 10 mmol) was added as an internal reference, the $^1$H-NMR spectrum was measured, and the structure and yield of the product were determined. These results are shown as Entry 1 in Table 2.

[Dimethyl(2-phenylethyl)silyl]-benzene (Compound (I) above)]:

$^1$H-NMR (400 MHz, CDCl$_3$) δ=0.19 (s, 6H, Si(C$\underline{H}_3$)$_2$), 0.98-1.07 (m, 2H, SiC$\underline{H}_2$), 2.49-2.59 (m, 2H, C$\underline{H}_2$C$_6$H$_5$), 7.02-7.11 (m, 3H, C$_6$H$_5$), 7.12-7.16 (m, 2H, C$_6$H$_5$), 7.24-7.31 (m, 3H, C$_6$H$_5$), 7.39-7.47 (m, 2H, C$_6$H$_5$).

[Dimethyl[(1E)-2-phenylethenyl]silyl]-benzene (Compound (II) above)]:

$^1$H-NMR (400 MHz, CDCl$_3$) δ=0.17 (s, 6H, Si(C$\underline{H}_3$)$_2$), 6.49 (d, J$_{H-H}$=19.3 Hz, 1H, SiC$\underline{H}$=CH—), 7.01-7.09 (m, 3H, C$_6$H$_5$), 7.12-7.15 (m, 3H, C$_6$H$_5$ and SiCH=C$\underline{H}$-), 7.25-7.32 (m, 3H, C$_6$H$_5$), 7.37-7.46 (m, 2H, C$_6$H$_5$).

[Working Example 13] Hydrosilylation Reaction Using Ruthenium Complex C

A magnetic stirrer was placed in a 20 mL Schlenk tube and the tube was dried by heating under a reduced pressure of 5 Pa, after which the tube interior was purged with argon. Ruthenium Complex C (3.9 mg, 0.005 mmol) was added as the catalyst to this Schlenk tube. Styrene (1,040 mg, 10 mmol) was added thereto, followed by dimethylphenylsilane (1,500 mg, 11 mmol), and the resulting solution was stirred at 25° C. for 23 hours. After cooling of the solution, anisole (1,080 mg, 10 mmol) was added as an internal reference, the $^1$H-NMR spectrum was measured, and the structure and yield of the product were determined. These results are shown as Entry 2 in Table 2.

[Working Example 14] Hydrosilylation Reaction Using Ruthenium Complex D

A magnetic stirrer was placed in a 20 mL Schlenk tube and the tube was dried by heating under a reduced pressure of 5 Pa, after which the tube interior was purged with argon. Ruthenium Complex D (0.9 mg, 0.001 mmol) was added as the catalyst to this Schlenk tube. Styrene (1,040 mg, 10 mmol) was added thereto, followed by dimethylphenylsilane (1,500 mg, 11 mmol), and the resulting solution was stirred at 25° C. for 23 hours. After cooling of the solution, anisole (1,080 mg, 10 mmol) was added as an internal reference, the $^1$H-NMR spectrum was measured, and the structure and yield of the product were determined. These results are shown as Entry 3 in Table 2.

[Working Example 15] Hydrosilylation Reaction Using Ruthenium Complex E

A magnetic stirrer was placed in a 20 mL Schlenk tube and the tube was dried by heating under a reduced pressure of 5 Pa, after which the tube interior was purged with argon. Ruthenium Complex E (8.1 mg, 0.01 mmol) was added as the catalyst to this Schlenk tube. Styrene (104 mg, 1.0 mmol) was added thereto, followed by dimethylphenylsilane (150 mg, 1.1 mmol), and the resulting solution was stirred at 25° C. for 23 hours. After cooling, anisole (108 mg, 1.0 mmol) was added as an internal reference, the $^1$H-NMR spectrum was measured, and the structure and yield of the product were determined. These results are shown as Entry 4 in Table 2.

TABLE 2

| Entry | Cat | Cat loading (X) (mol %) | Temp. (° C.) | Time (h) | Yield (I) | Yield (II) | Yield (III) |
|---|---|---|---|---|---|---|---|
| 1 | A | 0.05 | r.t. | 23 | 47 | 22 | 24 |
| 2 | C | 0.05 | r.t. | 23 | 70 | 15 | 15 |
| 3 | D | 0.01 | r.t. | 23 | 92 | 6 | 6 |
| 4 | E | 1 | r.t. | 23 | 5 | 6 | 49 |

(4) Hydrosilylation Reactions with 1,1,1,3,3-Pentamethyldisiloxane Using Ruthenium Complexes

[Chemical Formula 23]

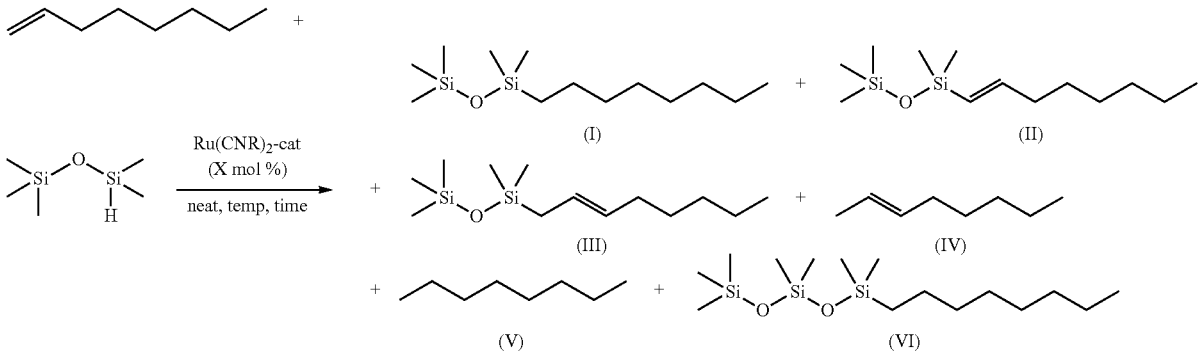

[Working Example 16] Hydrosilylation of 1-Octene with 1,1,1,3,3-Pentamethylsiloxane A magnetic stirrer was placed in a 20 mL Schlenk tube and the tube was dried by heating under a reduced pressure of 5 Pa, after which the tube interior was purged with argon. Ruthenium Complex A (2.0 mg, 0.003 mmol) was added as the catalyst to this Schlenk tube. 1-Octene (112 mg, 1.0 mmol) was added thereto, followed by 1,1,1,3,3-pentamethyldisiloxane (163 mg, 1.1 mmol), and the resulting solution was stirred at 80° C. for 23 hours. After cooling of the solution, anisole (108 mg, 1.0 mmol) was added as an internal reference, the $^1$H-NMR spectrum was measured, and the structure and yield of the product were determined. These results are shown as Entry 1 in Table 3.

[Working Example 17] Hydrosilylation Using Ruthenium Complex B

A magnetic stirrer was placed in a 20 mL Schlenk tube and the tube was dried by heating under a reduced pressure of 5 Pa, after which the tube interior was purged with argon. Ruthenium Complex B (2.4 mg, 0.003 mmol) was added as the catalyst to this Schlenk tube. 1-Octene (112 mg, 1.0 mmol) was added thereto, followed by 1,1,1,3,3-pentamethyldisiloxane (163 mg, 1.1 mmol), the resulting solution was stirred at 25° C. for 23 hours. After cooling of the solution, anisole (108 mg, 1.0 mmol) was added as an internal reference, the $^1$H-NMR spectrum was measured, and the structure and yield of the product were determined. These results are shown as Entry 2 in Table 3.

[Working Example 18] Hydrosilylation Using Ruthenium Complex C

A magnetic stirrer was placed in a 20 mL Schlenk tube and the tube was dried by heating under a reduced pressure of 5 Pa, after which the tube interior was purged with argon. Ruthenium Complex C (2.3 mg, 0.003 mmol) was added as the catalyst to this Schlenk tube. 1-Octene (112 mg, 1.0 mmol) was added thereto, followed by 1,1,1,3,3-pentamethyldisiloxane (163 mg, 1.1 mmol), and the resulting solution was stirred at 25° C. for 23 hours. After cooling of the solution, anisole (108 mg, 1.0 mmol) was added as an internal reference, the $^1$H-NMR spectrum was measured, and the structure and yield of the product were determined. These results are shown as Entry 3 in Table 3.

[Working Example 19] Hydrosilylation Using Ruthenium Complex D

A magnetic stirrer was placed in a 20 mL Schlenk tube and the tube was dried by heating under a reduced pressure of 5 Pa, after which the tube interior was purged with argon. Ruthenium Complex D (4.3 mg, 0.005 mmol) was added as the catalyst to this Schlenk tube. 1-Octene (112 mg, 1.0 mmol) was added thereto, followed by 1,1,1,3,3-pentamethyldisiloxane (163 mg, 1.1 mmol), and the resulting solution was stirred at 80° C. for 23 hours. After cooling of the solution, anisole (108 mg, 1.0 mmol) was added as an internal reference, the $^1$H-NMR spectrum was measured, and the structure and yield of the product were determined. These results are shown as Entry 4 in Table 3.

1,1,1,3,3-Pentamethyl-3-octyl-disiloxane (Compound (I) above):
$^1$H-NMR (400 MHz, CDCl$_3$) δ=0.03 (s, 6H, Si(CH$_3$)$_2$), 0.06 (s, 9H, Si(CH$_3$)$_3$), 0.45-0.55 (m, 2H, SiCH$_2$), 0.88 (t, $J_{HH}$=7.2 Hz, 3H, CH$_2$CH$_3$), 1.20-1.34 (m, 12H, (CH$_2$))$_6$).

1,1,1,3,3-Pentamethyl-3-(1E)-1-octen-1-yl-disiloxane (Compound (II) above):
$^1$H-NMR (400 MHz, CDCl$_3$) δ=0.09 (s, 9H, Si(CH$_3$)$_3$), 0.12 (s, 6H, Si(CH$_3$)$_2$), 0.90 (t, 3H, $J_{HH}$=7.6 Hz), 1.30-1.41 (m, 8H, CH$_2$), 2.11 (q, 2H, $J_{HH}$=7.6 Hz, CH$_2$—CH=CH), 5.6 (d, 1H, $J_{HH}$=18.2 Hz, Si—CH=CH), 6.11 (dt, 1H, $J_{HH}$=18.2 Hz, Si—CH=CH).

1,1,1,3,3-Pentamethyl-(2E)-2-octen-1-yl-disiloxane (Compound (III) above):
$^1$H-NMR (400 MHz, CDCl$_3$) δ=0.08 (s, 9H, Si(CH$_3$)$_2$), 0.14 (s, 6H, Si(CH$_3$)$_2$), 0.88 (t, 3H, $J_{HH}$=7.6 Hz), 1.28-1.42 (m, 8H, CH$_2$), 2.12 (q, 2H, $J_{HH}$=7.6 Hz, CH$_2$—CH=CH), 5.15-5.46 (m, 2H, Si—CH$_2$—CH=CH).

2-Octene (Compound (IV) above):
$^1$H-NMR (400 MHz, CDCl$_3$) δ=0.90 (t, $J_{HH}$=7.2 Hz, 3H, CH$_3$), 1.11-1.51 (m, 4H, —(CH$_2$)$_6$—), 1.54-1.62 (m, 5H, —(CH$_2$)$_6$— and CH$_3$—CH=CH), 2.03 (m, 2H, —CH$_2$—CH=CH), 5.19-5.66 (m, 2H, CH$_3$—CH=CH).

2-Octane (Compound (V) above):
$^1$H-NMR (400 MHz, CDCl$_3$) δ=0.88 (t, $J_{HH}$=7.2 Hz, 6H, CH$_3$), 1.16-1.36 (m, 12H, —(CH$_2$)$_6$—).

1,1,1,3,3,5,5-Heptamethyl-5-octyl-trisiloxane (Compound (VI) above):
$^1$H-NMR (400 MHz, CDCl$_3$) δ=−0.13 (s, 6H, —Si(CH$_3$)$_2$—), −0.13 (s, 6H, —Si(CH$_3$)$_2$—), 0.01 (s, 6H, —Si(CH$_3$)$_2$—), 0.31-0.38 (m, 2H, SiCH$_2$), 0.79 (t, $J_{HH}$=7.2 Hz, 3H, CH$_2$CH$_3$), 1.12-1.24 (m, 12H, (CH$_2$)$_6$).

[Working Example 20] Hydrosilylation Reaction Using Ruthenium Complex E

A magnetic stirrer was placed in a 20 mL Schlenk tube and the tube was dried by heating under a reduced pressure of 5 Pa, after which the tube interior was purged with argon. Ruthenium Complex E (24 mg, 0.03 mmol) was added as the catalyst to this Schlenk tube. 1-Octene (112 mg, 1.0 mmol) was added thereto, followed by 1,1,1,3,3-pentamethyldisiloxane (163 mg, 1.1 mmol), and the resulting solution was stirred at 80° C. for 23 hours. After cooling of the solution, anisole (108 mg, 1.0 mmol) was added as an internal reference, the $^1$H-NMR spectrum was measured, and the structure and yield of the product were determined. These results are shown as Entry 5 in Table 3.

[Working Example 21] Hydrosilylation Reaction Using Ruthenium Complex F

A magnetic stirrer was placed in a 20 mL Schlenk tube and the tube was dried by heating under a reduced pressure of 5 Pa, after which the tube interior was purged with argon. Ruthenium Complex F (2.3 mg, 0.003 mmol) was added as the catalyst to this Schlenk tube. 1-Octene (112 mg, 1.0 mmol) was added thereto, followed by 1,1,1,3,3-pentamethyldisiloxane (163 mg, 1.1 mmol), and the resulting solution was stirred at 25° C. for 23 hours. After cooling of the solution, anisole (108 mg, 1.0 mmol) was added as an internal reference, the $^1$H-NMR spectrum was measured, and the structure and yield of the product were determined. These results are shown as Entry 6 in Table 3.

TABLE 3

| Entry | Cat | Cat loading (X) (mol %) | Temp. (° C.) | Time (h) | Yield (I) | (II) | (III) | (IV) | (V) | (VI) |
|---|---|---|---|---|---|---|---|---|---|---|
| 1 | A | 0.3 | 80 | 23 | 4 | 9 | 5 | 50 | 0 | 0 |
| 2 | B | 0.3 | r.t. | 23 | 0 | 0 | 0 | 65 | 35 | 0 |
| 3 | C | 0.3 | r.t. | 23 | 0 | 0 | 0 | 65 | 35 | 0 |
| 4 | D | 0.5 | 80 | 23 | 33 | 0 | trace | 0 | 30 | 30 |
| 5 | E | 3 | 80 | 3 | 4 | 0 | 0 | 98 | 4 | 0 |
| 6 | F | 0.3 | r.t. | 23 | trace | 0 | 3 | 4 | 0 | 0 |

(5) Hydrogenation Reactions on 1-Octene Using Ruthenium Complexes

[Chemical Formula 24]

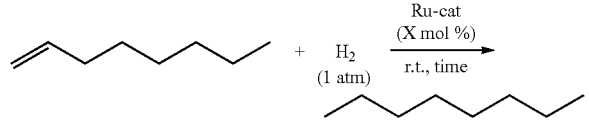

[Working Example 22] Hydrogenation Reaction Using Ruthenium Complex A

A magnetic stirrer was placed in a 20 mL Schlenk tube and the tube was dried by heating under a reduced pressure of 5 Pa, after which the tube interior was purged with argon. Ruthenium Complex A (3.3 mg, 0.005 mmol) was added as the catalyst to this Schlenk tube and dissolved in THF (2 mL). To this solution was added 1-octene (112 mg, 1.0 mmol). The resulting solution was freeze-pump-thaw degassed, the interior of the Schlenk tube was purged with hydrogen, and the solution was stirred at room temperature for 3 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 1 in Table 4.
$^1$H-NMR (400 MHz, CDCl$_3$) δ=0.88 (t, $J_{HH}$=7.2 Hz, 6H, CH$_3$), 1.16-1.36 (m, 12H, —(CH$_2$)$_6$—).
$^{13}$C-NMR (100 MHz, CDCl$_3$) δ=14.27, 22.86, 29.48, 32.10

[Working Example 23] Hydrogenation Reaction Using Ruthenium Complex B

A magnetic stirrer was placed in a 20 mL Schlenk tube and the tube was dried by heating under a reduced pressure of 5 Pa, after which the tube interior was purged with argon. Ruthenium Complex B (4.0 mg, 0.005 mmol) was added as the catalyst to this Schlenk tube and dissolved in THF (2 mL). To this solution was added 1-octene (112 mg, 1.0 mmol). The resulting solution was freeze-pump-thaw degassed, the interior of the Schlenk tube was purged with hydrogen, and the solution was stirred at room temperature for 3 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 2 in Table 4.

[Working Example 24] Hydrogenation Reaction Using Ruthenium Complex C

A magnetic stirrer was placed in a 20 mL Schlenk tube and the tube was dried by heating under a reduced pressure of 5 Pa, after which the tube interior was purged with argon. Ruthenium Complex C (3.9 mg, 0.005 mmol) was added as the catalyst to this Schlenk tube and dissolved in THF (2 mL). To this solution was added 1-octene (112 mg, 1.0 mmol). The resulting solution was freeze-pump-thaw degassed, the interior of the Schlenk tube was purged with hydrogen, and the solution was stirred at room temperature for 3 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 3 in Table 4.

[Working Example 25] Hydrogenation Reaction Using Ruthenium Complex D

A magnetic stirrer was placed in a 20 mL Schlenk tube and the tube was dried by heating under a reduced pressure of 5 Pa, after which the tube interior was purged with argon. Ruthenium Complex D (4.3 mg, 0.005 mmol) was added as the catalyst to this Schlenk tube and dissolved in THF (2 mL). To this solution was added 1-octene (112 mg, 1.0 mmol). The resulting solution was freeze-pump-thaw degassed, the interior of the Schlenk tube was purged with hydrogen, and the solution was stirred at room temperature for 6 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 4 in Table 4.

[Working Example 26] Hydrogenation Reaction Using Ruthenium Complex F

A magnetic stirrer was placed in a 20 mL Schlenk tube and the tube was dried by heating under a reduced pressure of 5 Pa, after which the tube interior was purged with argon. Ruthenium Complex F (3.8 mg, 0.005 mmol) was added as the catalyst to this Schlenk tube and dissolved in THF (2 mL). To this solution was added 1-octene (112 mg, 1.0 mmol). The resulting solution was freeze-pump-thaw degassed, the interior of the Schlenk tube was purged with hydrogen, and the solution was stirred at room temperature for 3 hours. Anisole (108 mg, 1.0 mmol) was added as an internal reference, the $^1$H-NMR spectrum was measured, and the structure and yield of the product were determined.

The structure of the resulting compound was confirmed from the $^1$H and $^{13}$C-NMR spectra. These results are shown as Entry 5 in Table 4.

TABLE 4

| Entry | Cat | Cat loading (X) (mol %) | Time (h) | Yield (%) |
|---|---|---|---|---|
| 1 | A | 0.5 | 3 | 64 |
| 2 | B | 0.5 | 3 | 27 |
| 3 | C | 0.5 | 3 | >99 |
| 4 | D | 0.5 | 6 | 80 |
| 5 | F | 0.5 | 3 | 87 |

(6) Styrene Hydrogenation Using Ruthenium Complexes

[Chemical Formula 25]

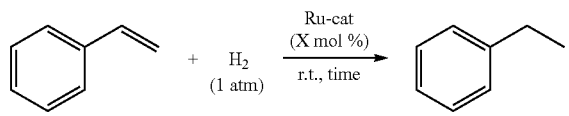

[Working Example 27] Hydrogenation Reaction Using Ruthenium Complex A

A magnetic stirrer was placed in a 20 mL Schlenk tube and the tube was dried by heating under a reduced pressure of 5 Pa, after which the tube interior was purged with argon. Ruthenium Complex A (0.65 mg, 0.001 mmol) was added as the catalyst to this Schlenk tube and dissolved in THF (2 mL). To this solution was added styrene (104 mg, 1.0 mmol). The resulting solution was freeze-pump-thaw degassed, the interior of the Schlenk tube was purged with hydrogen, and the solution was stirred at room temperature for 18 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 1 in Table 5.

$^1$H-NMR (400 MHz, CDCl$_3$) δ=1.13 (t, J$_{HH}$=7.2 Hz, 3H, CH$_2$CH$_3$), 2.54 (q, J$_{HH}$=7.2 Hz, 2H, CH$_2$CH$_3$), 7.02-7.11 (m, 3H, C$_6$H$_5$), 7.11-7.20 (m, 2H, C$_6$H$_5$).
$^{13}$C-NMR (100 MHz, CDCl$_3$) δ=15.6, 28.8, 125.6, 127.8, 128.3, 144.3

[Working Example 28] Hydrogenation Reaction Using Ruthenium Complex B

A magnetic stirrer was placed in a 20 mL Schlenk tube and the tube was dried by heating under a reduced pressure of 5 Pa, after which the tube interior was purged with argon. Ruthenium Complex B (0.8 mg, 0.001 mmol) was added as the catalyst to this Schlenk tube and dissolved in THF (2 mL). To this solution was added styrene (104 mg, 1.0 mmol). The resulting solution was freeze-pump-thaw degassed, the interior of the Schlenk tube was purged with hydrogen, and the solution was stirred at room temperature for 18 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 2 in Table 5.

[Working Example 29] Hydrogenation Reaction Using Ruthenium Complex C

A magnetic stirrer was placed in a 20 mL Schlenk tube and the tube was dried by heating under a reduced pressure of 5 Pa, after which the tube interior was purged with argon. Ruthenium Complex C (0.77 mg, 0.001 mmol) was added as the catalyst to this Schlenk tube and dissolved in toluene (2 mL). To this solution was added styrene (104 mg, 1.0 mmol). The resulting solution was freeze-pump-thaw degassed, the interior of the Schlenk tube was purged with hydrogen, and the solution was stirred at room temperature for 6 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 3 in Table 5.

[Working Example 30] Hydrogenation Reaction Using Ruthenium Complex D

A magnetic stirrer was placed in a 20 mL Schlenk tube and the tube was dried by heating under a reduced pressure of 5 Pa, after which the tube interior was purged with argon. Ruthenium Complex D (0.86 mg, 0.001 mmol) was added as the catalyst to this Schlenk tube and dissolved in THF (2 mL). To this solution was added styrene (104 mg, 1.0 mmol). The resulting solution was freeze-pump-thaw degassed, the interior of the Schlenk tube was purged with hydrogen, and the solution was stirred at room temperature for 18 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 4 in Table 5.

[Working Example 31] Hydrogenation Reaction Using Ruthenium Complex E

A magnetic stirrer was placed in a 20 mL Schlenk tube and the tube was dried by heating under a reduced pressure of 5 Pa, after which the tube interior was purged with argon. Ruthenium Complex E (2.44 mg, 0.003 mmol) was added as the catalyst to this Schlenk tube and dissolved in THF (2 mL). To this solution was added styrene (104 mg, 1.0 mmol). The resulting solution was freeze-pump-thaw degassed, the interior of the Schlenk tube was purged with hydrogen, and the solution was stirred at room temperature for 1.5 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 5 in Table 5.

[Working Example 32] Hydrogenation Reaction Using Ruthenium Complex F

A magnetic stirrer was placed in a 20 mL Schlenk tube and the tube was dried by heating under a reduced pressure of 5 Pa, after which the tube interior was purged with argon. Ruthenium Complex F (0.76 mg, 0.001 mmol) was added as the catalyst to this Schlenk tube and dissolved in THF (2 mL). To this solution was added styrene (104 mg, 1.0 mmol). The resulting solution was freeze-pump-thaw degassed, the interior of the Schlenk tube was purged with hydrogen, and the solution was stirred at room temperature for 6 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 6 in Table 5.

TABLE 5

| Entry | Alkene | Cat | Cat loading (X) (mol %) | Time (h) | Yield (%) |
|---|---|---|---|---|---|
| 1 | styrene | A | 0.1 | 18 | 5 |
| 2 | | B | 0.1 | 18 | 8 |
| 3 | | C | 0.1 | 6 | >99 |
| 4 | | D | 0.1 | 18 | 77 |
| 5 | | E | 0.3 | 1.5 | 75 |
| 6 | | F | 0.1 | 6 | 47 |

(7) Olefin Hydrogenation Using Ruthenium Complex C

[Chemical Formula 26]

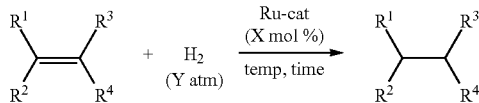

[Working Example 33] Hydrogenation of Methyl-10-Undecenoate

A magnetic stirrer was placed in a 20 mL Schlenk tube and the tube was dried by heating under a reduced pressure of 5 Pa, after which the tube interior was purged with argon. Ruthenium Complex C (3.9 mg, 0.005 mmol) was added as the catalyst to this Schlenk tube and dissolved in toluene (2 mL) To this solution was added methyl-10-undecenoate (198 mg, 1.0 mmol). The resulting solution was freeze-pump-thaw degassed, the interior of the Schlenk tube was purged with hydrogen, and the solution was stirred at room temperature for 1.5 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 1 in Table 6.

$^1$H-NMR (400 MHz, CDCl$_3$) δ=0.88 (t, 3H, $J_{HH}$=7.4 Hz, —CH$_2$), 1.17-1.35 (m, 14H, —CH$_2$—), 1.53-1.67 (m, 2H, —CH$_2$—), 2.30 (t, 2H, $J_{HH}$=7.7 Hz, —CH$_2$C(=O)—), 3.66 (s, 3H, OMe).

$^{13}$C-NMR (100 MHz, CDCl$_3$) δ=14.25, 22.83, 25.12, 29.31, 29.40, 29.45, 29.60, 29.70, 32.04, 34.28, 51.57, 174.50.

[Working Example 34] Hydrogenation of Cyclohexene

A magnetic stirrer was placed in a 20 mL Schlenk tube and the tube was dried by heating under a reduced pressure of 5 Pa, after which the tube interior was purged with argon. Ruthenium Complex C (2.3 mg, 0.003 mmol) was added as the catalyst to this Schlenk tube and dissolved in toluene (2 mL). To this solution was added cyclohexene (82 mg, 1.0 mmol). The resulting solution was freeze-pump-thaw degassed, the interior of the Schlenk tube was purged with hydrogen, and the solution was stirred at room temperature for 4 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 2 in Table 6.

$^1$H-NMR (400 MHz, CDCl$_3$) δ=1.43 (s, 12H, CH$_2$).
$^{13}$C-NMR (100 MHz, CDCl$_3$) δ=27.0.

[Working Example 35] Hydrogenation of Ethyl 2,3-Dimethylacrylate

A magnetic stirrer was placed in a 20 mL Schlenk tube and the tube was dried by heating under a reduced pressure of 5 Pa, after which the tube interior was purged with argon. Ruthenium Complex C (2.3 mg, 0.003 mmol) was added as the catalyst to this Schlenk tube and dissolved in toluene (2 mL). To this solution was added ethyl 2,3-dimethylacrylate (128 mg, 1.0 mmol). The resulting solution was freeze-pump-thaw degassed, the interior of the Schlenk tube was purged with hydrogen, and the solution was stirred at room temperature for 6 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 3 in Table 6.

$^1$H-NMR (400 MHz, CDCl$_3$) δ=0.93-0.96 (m, 6H, Me), 1.28 (t, 3H, OCH$_2$C$\underline{H}_2$), 2.00-2.04 (m, 1H, CH and CH$_2$C(=O)), 4.19 (q, 2H, OC$\underline{H}_2$CH$_3$).

$^{13}$C-NMR (100 MHz, CDCl$_3$) δ=14.6, 22.9, 26.0, 43.6, 60.3, 173.5.

[Working Example 36] Hydrogenation of 2,3-Dimethyl-2-butene

A magnetic stirrer was placed in a 20 mL Schlenk tube and the tube was dried by heating under a reduced pressure of 5 Pa, after which the tube interior tube was purged with argon. Ruthenium Complex C (3.9 mg, 0.005 mmol) was added as the catalyst to this Schlenk tube and dissolved in toluene (2 mL). To this solution was added 2,3-dimethyl-2-butene (84 mg, 1.0 mmol). The resulting solution was freeze-pump-thaw degassed, the interior of the Schlenk tube was purged with hydrogen, and the solution was stirred at room temperature for 6 hours. Anisole (108 mg, 1.0 mmol) was added as an internal reference, the $^1$H-NMR spectrum was measured, and the structure and yield of the product were determined. The structure of the resulting compound was confirmed from the $^1$H and $^{13}$C-NMR spectra. These results are shown as Entry 4 in Table 6.

$^1$H-NMR (400 MHz, CDCl$_3$) δ=0.84 (d, $J_{H\text{-}H}$=6.7 Hz, 12H, CH$_3$), 1.40 (septet, $J_{H\text{-}H}$=6.7 Hz, 12H, CH).
$^{13}$C-NMR (100 MHz, CDCl$_3$) δ=19.4, 33.7.

[Working Example 37] Hydrogenation of Trans-Stilbene

A magnetic stirrer was placed in a 20 mL Schlenk tube and the tube was dried by heating under a reduced pressure of 5 Pa, after which the tube interior was purged with argon. Ruthenium Complex C (2.3 mg, 0.003 mmol) was added as the catalyst to this Schlenk tube and dissolved in toluene (2 mL). To this solution was added trans-stilbene (180 mg, 1.0 mmol). The resulting solution was freeze-pump-thaw degassed, the interior of the Schlenk tube was purged with hydrogen, and the solution was stirred at room temperature for 6 hours. Anisole was added as an internal reference, the $^1$H-NMR spectrum was measured, and the structure and yield of the product were determined. The structure of the resulting compound was confirmed from the $^1$H and $^{13}$C-NMR spectra. These results are shown as Entry 5 in Table 6.

$^1$H-NMR (400 MHz, CDCl$_3$) δ=2.93 (s, 4H, CH$_2$), 7.12-7.23 (m, 6H, C$_6$H$_5$), 7.24-7.32 (m, 4H, C$_6$H$_5$).

$^{13}$C-NMR (100 MHz, CDCl$_3$) δ=37.9, 125.9, 128.3, 128.5, 141.8.

[Working Example 38] Hydrogenation of 1-Methyl-1-Cyclohexene

A magnetic stirrer was placed in a 20 mL Schlenk tube and the tube was dried by heating under a reduced pressure of 5 Pa, after which the tube interior was purged with argon. Ruthenium Complex C (2.3 mg, 0.003 mmol) was added as the catalyst to this Schlenk tube and dissolved in toluene (2 mL) To this solution was added 1-methyl-1-cyclohexene (96 mg, 1.0 mmol). The resulting solution was freeze-pump-thaw degassed, the interior of the Schlenk tube was purged with hydrogen, and the solution was stirred at room temperature for 3 hours. Anisole was added as an internal reference, the $^1$H-NMR spectrum was measured, and the structure and yield of the product were determined. The structure of the resulting compound was confirmed from the $^1$H and $^{13}$C-NMR spectra. These results are shown as Entry 6 in Table 6.

$^1$H-NMR (400 MHz, CDCl$_3$) δ=0.86 (d, J$_{HH}$=5.8 Hz, 3H, CH$_3$), 1.04-1.28 (m, 4H, CH$_2$), 1.28-1.39 (m, 1H, CH), 1.54-1.72 (m, 6H, CH$_2$).

$^{13}$C-NMR (100 MHz, CDCl$_3$) δ=22.9, 26.3, 26.4, 32.7, 35.4.

[Working Example 39] Hydrogenation of (±)-Limonene

A magnetic stirrer was placed in a 20 mL Schlenk tube and the tube was dried by heating under a reduced pressure of 5 Pa, after which the tube interior was purged with argon. Ruthenium Complex C (7.7 mg, 0.010 mmol) was added as the catalyst to this Schlenk tube and dissolved in toluene (2 mL). To this solution was added (±)-limonene (136 mg, 1.0 mmol). The resulting solution was transferred to an autoclave and the interior of the autoclave was purged with hydrogen. Next, the solution was stirred for 6 hours at room temperature under a hydrogen atmosphere at a pressure of 10 atmospheres. Anisole was added as an internal reference, the $^1$H-NMR spectrum was measured, and the structure and yield of the product were determined. The structure of the resulting compound was confirmed from the 1H and $^{13}$C-NMR spectra (trans:cis=1:1) These results are shown as Entry 7 in Table 6.

$^1$H-NMR (400 MHz, CDCl$_3$) δ=0.847 (d, 2H, J$_{HH}$=6.8 Hz, CH(CH$_3$)$_2$ of trans-isomer), 0.859 (d, 3H, J$_{HH}$=6.8 Hz, CH$_3$ of trans-isomer), 0.860 (d, 2H, J$_{HH}$=6.8 Hz, CH(CH$_3$)$_2$ of cis-isomer), 0.909 (d, 3H, J$_{HH}$=6.8 Hz, CH$_3$ of cis-isomer), 0.87-1.09 (m, 2H, CH and CH$_2$), 1.18-1.58 (m, 6H, CH and CH$_2$), 1.62-1.77 (m, 3H, CH$_2$).

$^{13}$C-NMR (100 MHz, CDCl$_3$) δ=19.5, 20.0, 20.4, 22.9, 25.5, 29.3, 29.7, 31.6, 33.0, 33.1, 35.8, 43.2, 44.0.

[Working Example 40] Hydrogenation of Diethyl Isopropylidenemalonate

A magnetic stirrer was placed in a 20 mL Schlenk tube and the tube was dried by heating under a reduced pressure of 5 Pa, after which the tube interior was purged with argon. Ruthenium Complex C (7.7 mg, 0.010 mmol) was added as the catalyst to this Schlenk tube and dissolved in toluene (2 mL). To this solution was added diethyl isopropylidenemalonate (200 mg, 1.0 mmol). The resulting solution was transferred to an autoclave and the interior of the autoclave was purged with hydrogen. Next, the solution was stirred for 9 hours at room temperature under a hydrogen atmosphere at a pressure of 10 atmospheres. Anisole was added as an internal reference, the $^1$H-NMR spectrum was measured, and the structure and yield of the product were determined. The structure of the resulting compound was confirmed from the $^1$H and $^{13}$C-NMR spectra. These results are shown as Entry 8 in Table 6.

$^1$H-NMR (400 MHz, CDCl$_3$) δ=0.99 (d, J$_{HH}$=6.3 Hz, 3H, CH$_3$), 1.26 (t, J$_{HH}$=7.3 Hz, 3H, CH$_3$), 2.38 (doublet of septet, J$_{HH}$=6.3, 8.7 Hz, 1H, CHMe$_2$), 3.10 (d, J$_{HH}$=8.7 Hz, 1H, Me$_2$CH—CH—), 4.82 (q, J$_{HH}$=7.3 Hz, 2H, CH$_2$).

$^{13}$C-NMR (100 MHz, CDCl$_3$) δ=14.3, 20.5, 28.9, 59.3, 61.3, 169.0

[Working Example 41] Hydrogenation of 2,3-Dimethyl-1H-Indene

A magnetic stirrer was placed in a 20 mL Schlenk tube and the tube was dried by heating under a reduced pressure of 5 Pa, after which the tube interior was purged with argon. Ruthenium Complex C (7.7 mg, 0.010 mmol) was added as the catalyst to this Schlenk tube and dissolved in toluene (2 mL) To this solution was added 2,3-dimethyl-1H-indene (144 mg, 1.0 mmol). The resulting solution was transferred to an autoclave and the interior of the autoclave was purged with hydrogen. Next, the solution was stirred for 6 hours at 80° C. under a hydrogen atmosphere at a pressure of 10 atmospheres. Anisole was added as an internal reference, the $^1$H-NMR spectrum was measured, and the structure and yield of the product were determined. The structure of the resulting compound was confirmed from the $^1$H and $^{13}$C-NMR spectra. These results are shown as Entry 9 in Table 6.

$^1$H-NMR (400 MHz, CDCl$_3$) δ=0.94 (d, 3H, J=6.9 Hz, CH$_3$CHCH$_2$), 1.14 (d, 3H, J=7.2 Hz, CH$_3$CH), 2.49-2.61 (m, 2H), 2.94 (m, 1H), 3.17 (quintet, 1H, J=6.9 Hz, CH$_3$CH), 7.06-7.24 (m, 4H, C$_6$H$_4$).

$^{13}$C-NMR (100 MHz, CDCl$_3$) δ=14.5, 15.0, 37.8, 39.2, 42.6, 123.5, 124.3, 126.0, 126.1, 142.8, 149.0.

[Working Example 42] Hydrogenation of Cinnamyl Acetate

A magnetic stirrer was placed in a 20 mL Schlenk tube and the tube was dried by heating under a reduced pressure of 5 Pa, after which the tube interior was purged with argon. Ruthenium Complex C (7.7 mg, 0.010 mmol) was added as the catalyst to this Schlenk tube and dissolved in toluene (2 mL). To this solution was added cinnamyl acetate (176 mg, 1.0 mmol). The resulting solution was transferred to an autoclave and the interior of the autoclave was purged with hydrogen. Next, the solution was stirred for 6 hours at room temperature under a hydrogen atmosphere at a pressure of 10 atmospheres. Anisole was added as an internal reference, the $^1$H-NMR spectrum was measured, and the structure and yield of the product were determined. The structure of the resulting compound was confirmed from the $^1$H and $^{13}$C-NMR spectra. These results are shown as Entry 10 in Table 6.

$^1$H-NMR (400 MHz, CDCl$_3$) δ=1.96 (m, 2H, PhCH$_2$CH$_2$CH$_2$—), 2.06 (s, 3H, Me), 2.70 (m, 2H, 2H, PhCH$_2$CH$_2$CH$_2$—), 4.09 (t, 2H, J=6.8 Hz, PhCH$_2$CH$_2$CH$_2$—), 7.17-7.23 (m, 3H, Ph), 7.27-7.32 (m, 2H, Ph).

$^{13}$C-NMR (100 MHz, CDCl$_3$) δ=21.1, 30.3, 32.3, 64.0, 126.2, 128.5, 128.6, 141.3, 171.3.

TABLE 6

| Entry | Alkene | Cat loading (X) (mol %) | H$_2$ (Y) (atm) | Temp. (° C.) | Time (h) | Yield (%) |
|---|---|---|---|---|---|---|
| 1 | | 0.5 | 1 | 25 | 1.5 | >99 |
| 2 | | 0.3 | 1 | 25 | 4 | >99 |
| 3 | | 0.3 | 1 | 25 | 6 | >99 |
| 4 | | 0.5 | 1 | 25 | 6 | >99 |
| 5 | | 0.3 | 1 | 25 | 6 | >99 |
| 6 | | 0.3 | 1 | 25 | 3 | >99 |
| 7 | | 1 | 10 | 25 | 6 | >99 |
| 8 | | 1 | 10 | 25 | 9 | >99 |
| 9 | | 1 | 10 | 80 | 6 | >99 |
| 10 | | 1 | 10 | 25 | 6 | >99 |

(8) Reduction of N,N-Dimethylformamide Using Ruthenium Complexes

[Chemical Formula 27]

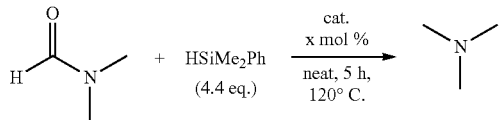

[Working Example 43] Reaction Using Ruthenium Complex C

An NMR tube was dried by heating under a reduced pressure of 5 Pa, following which Ruthenium Complex C (39 mg, 0.05 mmol) was added as the catalyst and 0.4 mL of heavy benzene was added by syringe. Dimethylphenylsilane (600 mg, 4.4. mmol) was subsequently added and N,N-dimethylformamide (73 mg, 1.0 mmol, abbreviated below as "DMF") was also added, after which the NMR tube was cut with a torch under reduced pressure to form a vacuum-sealed tube. The solution was stirred for 5 hours at 120° C., following which amine formation was confirmed from the $^1$H-NMR spectrum. These results are shown as Entry 1 in Table 7.

$^1$H-NMR (400 MHz, CDCl$_3$) δ=2.12 (s, 9H, NMe$_2$).

[Working Example 44] Reaction Using Ruthenium Complex E

An NMR tube was dried by heating under a reduced pressure of 5 Pa, following which Ruthenium Complex E (4.1 mg, 0.005 mmol) was added as the catalyst and 0.4 mL of heavy benzene was added by syringe. Dimethylphenylsilane (600 mg, 4.4. mmol) was subsequently added and DMF (73 mg, 1.0 mmol) was also added, after which the NMR tube was cut with a torch under reduced pressure to form a vacuum-sealed tube. The solution was stirred for 5 hours at 120° C., following which amine formation was confirmed from the $^1$H-NMR spectrum. These results are shown as Entry 2 in Table 7.

[Working Example 45] Reaction Using Ruthenium Complex F

An NMR tube was dried by heating under a reduced pressure of 5 Pa, following which Ruthenium Complex F (38 mg, 0.05 mmol) was added as the catalyst and 0.4 mL of heavy benzene was added by syringe. Dimethylphenylsilane (600 mg, 4.4. mmol) was subsequently added and DMF (73 mg, 1.0 mmol) was also added, after which the NMR tube was cut with a torch under reduced pressure to form a vacuum-sealed tube. The solution was stirred for 5 hours at 120° C., following which amine formation was confirmed from the $^1$H-NMR spectrum. These results are shown as Entry 3 in Table 7.

TABLE 7

| Entry | Cat | Cat loading (X) (mol %) | Yield (%) |
|---|---|---|---|
| 1 | C | 5 | >99 |
| 2 | E | 0.5 | 40 |
| 3 | F | 5 | >99 |

The invention claimed is:

1. A neutral or cationic mononuclear divalent ruthenium complex which is characterized by having formula (2)

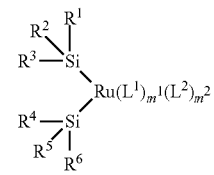

(2)

wherein R$^1$ to R$^6$ are each independently an alkyl, aryl, or aralkyl group, wherein any of R$^1$ to R$^6$ bond together to form a crosslinking substituent selected from the group consisting of —C═C—, an alkylene group of 1 to 10 carbon atoms, and an arylene group of 6 to 30 carbon atoms;

L$^1$ is at least one type of two-electron ligand selected from the group consisting of isonitriles, nitrogen-containing heterocycles, and phosphites, with the proviso that when a plurality of L$^1$ ligands are present, two L$^1$ ligands may be bonded to one another;

said isonitriles are represented by the formula RNC, wherein R is a substituted or unsubstituted alkyl group of 1 to 30 carbon atoms, aryl group of 6 to 30 carbon atoms or aralkyl group of 7 to 30 carbon atoms, said phosphites are represented by the formula (RO)$_3$P, wherein each R is independently as defined above, said nitrogen-containing heterocycles are at least one selected from the group consisting of pyrroles, imidazoles, pyridines, pyrimidines, oxazolines and isooxazolines;

L$^2$ is a two-electron ligand represented by the formula H—SiR$^7$R$^8$R$^9$ or H—SiR$^{10}$R$^{11}$R$^{12}$, wherein R$^7$ to R$^{12}$ are each independently an alkyl, aryl or aralkyl group; any of R$^7$ to R$^{12}$ may bond together to form a crosslinking substituent selected from the group consisting of —O—, an alkylene group of 1 to 10 carbon atoms and o-phenylene group which may be substituted with Y, wherein Y is a halogen atom, an alkyl group of 1 to 10 carbon atoms, or an alkoxy group of 1 to 10 carbon atoms, with the proviso that when a plurality of Y are present, they may be the same or different; and m$^1$ and m$^2$ are both 2.

2. The neutral or cationic mononuclear divalent ruthenium complex of claim 1, wherein L$^2$ is a two-electron ligand represented by the formula H—SiR$^7$R$^8$R$^9$ or H—SiR$^{10}$R$^{11}$R$^{12}$, wherein R$^7$ to R$^{12}$ are each independently an alkyl, aryl or aralkyl group, wherein any of R$^7$ to R$^{12}$ bond together to form an o-phenylene group which may be substituted with Y.

3. The neutral or cationic mononuclear divalent ruthenium complex of claim 2, wherein R$^7$ to R$^{12}$ are each independently an alkyl group of 1 to 10 carbon atoms or aryl group of 6 to 20 carbon atoms, wherein any of $R^7$ to $R^{12}$ bond together to form an o-phenylene group.

4. The neutral or cationic mononuclear divalent ruthenium complex of claim 1, wherein $R^1$ to $R^6$ are each independently an alkyl group of 1 to 10 carbon atoms or aryl group of 6 to 20 carbon atoms, wherein any of $R^1$ to $R^6$ bond together to form an o-phenylene group.

5. The neutral or cationic mononuclear divalent ruthenium complex of claim 1, wherein
any two of $R^1$ to $R^3$ are methyl groups, any two of $R^4$ to $R^6$ are methyl groups, and any of $R^1$ to $R^6$ bond together to form an o-phenylene group;
any two of $R^7$ to $R^9$ are methyl groups, any two of $R^{10}$ to $R^{12}$ are methyl groups, and any of $R^7$ to $R^{12}$ bond together to form an o-phenylene group.

6. The neutral or cationic mononuclear divalent ruthenium complex of claim 1, wherein
said isonitriles are represented by the formula RNC, wherein R is an alkyl group of 1 to 10 carbon atoms or a phenyl group substituted with an alkyl group of 1 to 10 carbon atoms,
said phosphites are represented by the formula (RO)$_3$P, wherein each R is an alkyl group of 1 to 10 carbon atoms,
said nitrogen-containing heterocycles are pyridines.

7. The neutral or cationic mononuclear divalent ruthenium complex of claim 6, wherein said isonitriles are at least one selected from the group consisting of methyl isocyanide, ethyl isocyanide, n-propyl isocyanide, cyclopropyl isocyanide, n-butyl isocyanide, isobutyl isocyanide, sec-butyl isocyanide, t-butyl isocyanide, n-pentyl isocyanide, isopentyl isocyanide, neopentyl isocyanide, n-hexyl isocyanide, cyclohexyl isocyanide, cycloheptyl isocyanide, 1,1-dimethylhexyl isocyanide, 1-adamantyl isocyanide, 2-adamantyl isocyanide, phenyl isocyanide, 2-methylphenyl isocyanide, 4-methylphenyl isocyanide, 2,4-dimethylphenyl isocyanide, 2,5-dimethylphenyl isocyanide, 2,6-dimethylphenyl isocyanide, 2,4,6-trimethylphenyl isocyanide, 2,4,6-tri-t-butylphenyl isocyanide, 2,6-diisopropylphenyl isocyanide, 1-naphthyl isocyanide, 2-naphthyl isocyanide, 2-methyl-1-naphthyl isocyanide, benzyl isocyanide and phenylethyl isocyanide.

8. The neutral or cationic mononuclear divalent ruthenium complex of claim 6, wherein said nitrogen-containing heterocycles are at least one selected from the group consisting of pyridine, 2-methylpyridine, 3-methylpyridine, 4-methylpyridine and 2,6-dimethylpyridine; and bipyridines such as 2,2'-bipyridine, 4,4'-dimethyl-2,2'-bipyridine, 5,5'-dimethyl-2,2'-bipyridine, 4,4'-diethyl-2,2'-bipyridine and 4,4'-di-tert-butyl-2,2'-bipyridine.

9. The neutral or cationic mononuclear divalent ruthenium complex of claim 6, wherein said phosphites are at least one selected from the group consisting of trimethylphosphite, triethylphosphite, triisopropylphosphite, tri-n-butylphosphite, tris(2-ethylhexyl)phosphite, tri-n-decylphosphite, 4-methyl-2,6,7-trioxa-1-phosphabicyclo[2.2.2]octane and 4-ethyl-2,6,7-trioxa-1-phosphabicyclo[2.2.2]octane.

10. A catalyst which comprises the neutral or cationic mononuclear divalent ruthenium complex of claim 1 having activity in at least one reaction selected from the group consisting of hydrosilylation reactions, hydrogenation reactions and carbonyl compound reduction reactions.

11. A method for preparing an addition compound, characterized by comprising the step of hydrosilylating an aliphatic unsaturated bond-containing compound with a Si—H bond-containing hydrosilane or organohydropolysiloxane in the presence of the catalyst of claim 10.

12. A method for preparing an alkane compound, characterized by comprising the step of hydrogenating a compound having an aliphatic unsaturated bond in the presence of the catalyst of claim 10.

13. A method for preparing an amine compound, characterized by comprising the step of reducing an amide compound with a Si—H bond-containing silane or organohydropolysiloxane in the presence of the catalyst of claim 10.

* * * * *